(12) United States Patent
Shibahara

(10) Patent No.: US 11,807,648 B2
(45) Date of Patent: Nov. 7, 2023

(54) PROCESS FOR PREPARING SUBSTITUTED POLYCYCLIC PYRIDONE DERIVATIVE AND CRYSTAL THEREOF

(71) Applicant: Shionogi & Co., Ltd., Osaka (JP)

(72) Inventor: Setsuya Shibahara, Amagasaki (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 17/578,743

(22) Filed: Jan. 19, 2022

(65) Prior Publication Data

US 2022/0251107 A1 Aug. 11, 2022

Related U.S. Application Data

(62) Division of application No. 16/310,897, filed as application No. PCT/JP2017/022478 on Jun. 19, 2017, now Pat. No. 11,261,198.

(30) Foreign Application Priority Data

Jun. 20, 2016 (JP) ................................. 2016-121453

(51) Int. Cl.
C07D 498/14 (2006.01)

(52) U.S. Cl.
CPC ........ *C07D 498/14* (2013.01); *C07B 2200/13* (2013.01)

(58) Field of Classification Search
CPC .................................................. C07D 498/14
USPC ........................................................ 544/101
See application file for complete search history.

(56) References Cited

U.S. PATENT DOCUMENTS

| | | | |
|---|---|---|---|
| 8,927,710 B2 | 1/2015 | Akiyama et al. | |
| 8,987,441 B2 | 3/2015 | Takahashi et al. | |
| 9,758,515 B2 | 9/2017 | Takahashi et al. | |
| 9,815,835 B2 | 11/2017 | Akiyama et al. | |
| 9,862,675 B1 | 1/2018 | Al-Ahmed et al. | |
| 10,202,379 B2 | 2/2019 | Takahashi et al. | |
| 10,392,406 B2 | 8/2019 | Kawai | |
| 10,633,397 B2 | 4/2020 | Kawai | |
| 10,759,814 B2 | 9/2020 | Kawai | |
| 2009/0270247 A1 | 10/2009 | Rhodes et al. | |
| 2013/0090439 A1 | 4/2013 | Lu et al. | |
| 2014/0107303 A1 | 4/2014 | Okamoto et al. | |
| 2016/0152738 A1 | 6/2016 | Jingwen et al. | |
| 2020/0247818 A1 | 8/2020 | Okamoto et al. | |
| 2020/0283455 A1 | 9/2020 | Kawai et al. | |
| 2020/0361958 A1 | 11/2020 | Kawai et al. | |

FOREIGN PATENT DOCUMENTS

| | | |
|---|---|---|
| CN | 1253958 | 5/2000 |
| CN | 1324886 | 12/2001 |
| CN | 101462922 | 6/2009 |
| CN | 102796208 | 11/2012 |
| CN | 103012750 | 4/2013 |
| CN | 103351443 | 10/2013 |
| CN | 103965450 | 8/2014 |
| CN | 104098481 | 10/2014 |
| CN | 104292407 | 1/2015 |
| CN | 104610479 | 5/2015 |
| CN | 105131257 | 12/2015 |
| CN | 105820317 | 8/2016 |
| CN | 106519084 | 3/2017 |
| EP | 0 962 465 | 12/1999 |
| EP | 1 514 873 | 3/2005 |
| EP | 2 412 709 | 2/2012 |
| EP | 2 444 400 | 4/2012 |
| EP | 2 620 436 | 7/2013 |

(Continued)

OTHER PUBLICATIONS

International Search Report dated Aug. 29, 2017 in corresponding International (PCT) Application No. PCT/JP2017/022478.

(Continued)

*Primary Examiner* — Kahsay Habte
(74) *Attorney, Agent, or Firm* — Wenderoth, Lind & Ponack, L.L.P.

(57) ABSTRACT

The present invention provides a process for preparing a compound of the formula (II):

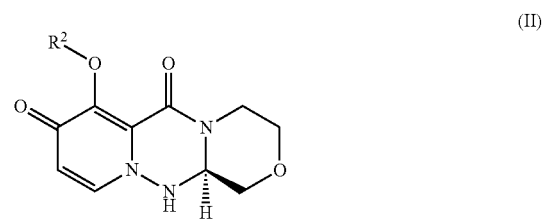

wherein $R^2$ is unsubstituted alkyl,
characterized by reacting a compound of the formula (I):

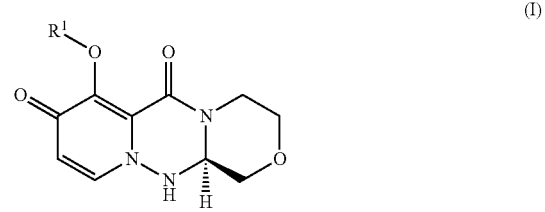

wherein $R^1$ is hydrogen or a protecting group other than unsubstituted alkyl,
with a compound of the formula: $R^2$—OH, wherein $R^2$ is as defined above, in the presence of a sodium salt and/or a magnesium salt.

5 Claims, 7 Drawing Sheets

(56) References Cited

FOREIGN PATENT DOCUMENTS

| | | |
|---|---|---|
| EP | 3 018 150 | 5/2016 |
| EP | 3 290 424 | 3/2018 |
| EP | 3 391 888 | 10/2018 |
| JP | 2012-077106 | 4/2012 |
| JP | 2014-513137 | 5/2014 |
| JP | 2016-166287 | 9/2016 |
| JP | 2016-169258 | 9/2016 |
| KR | 10-2009-0068772 | 6/2009 |
| KR | 10-2015-0034447 | 4/2015 |
| KR | 10-2016-0041144 | 4/2016 |
| WO | 94/07928 | 4/1994 |
| WO | 97/26297 | 7/1997 |
| WO | 02/053607 | 7/2002 |
| WO | 2008/037440 | 4/2008 |
| WO | 2008/143850 | 11/2008 |
| WO | 2009/132240 | 10/2009 |
| WO | 2010/110409 | 9/2010 |
| WO | 2010/147068 | 12/2010 |
| WO | 2012/007758 | 1/2012 |
| WO | 2012/039414 | 3/2012 |
| WO | 2012/109256 | 8/2012 |
| WO | 2012/151525 | 11/2012 |
| WO | 2012/165194 | 12/2012 |
| WO | 2013/052790 | 4/2013 |
| WO | 2015/124272 | 8/2015 |
| WO | 2016/080839 | 5/2016 |
| WO | 2016/109216 | 7/2016 |
| WO | 2016/175224 | 11/2016 |
| WO | 2017/087597 | 5/2017 |
| WO | 2017/087619 | 5/2017 |
| WO | 2017/104691 | 6/2017 |
| WO | 2018/030463 | 2/2018 |
| WO | 2019/070059 | 4/2019 |

OTHER PUBLICATIONS

International Preliminary Report dated Dec. 25, 2018 in corresponding International (PCT) Application No. PCT/JP2017/022478.
Greene's protective groups in organic synthesis—Fifth edition, pp. 27-31, 97-99, 475-489, 503-507, 2014.
Extended European Search Report dated Jan. 2, 2020 in European Patent Application No. 17815337.5.
Extended European Search Report dated Feb. 22, 2023 in corresponding European Patent Application No. 22206730.8.

| Time | Plasma concentration (ng/mL) | | | |
|---|---|---|---|---|
| (hr) | 0.3 mg/kg | 1 mg/kg | 3 mg/kg | 10 mg/kg |
| 0.25 | BLQ | BLQ | BLQ | BLQ |
| 0.5 | BLQ | BLQ | BLQ | BLQ |
| 1 | BLQ | BLQ | BLQ | BLQ |
| 2 | BLQ | BLQ | BLQ | BLQ |
| 4 | BLQ | BLQ | BLQ | BLQ |
| 6 | BLQ | BLQ | BLQ | BLQ |
| 8 | BLQ | BLQ | BLQ | BLQ |
| 10 | BLQ | BLQ | BLQ | BLQ |
| 24 | BLQ | BLQ | BLQ | BLQ |

BLQ : below the lower limit of quantification (< 0.500 ng/mL)

PROCESS FOR PREPARING SUBSTITUTED POLYCYCLIC PYRIDONE DERIVATIVE AND CRYSTAL THEREOF

This application is a divisional of U.S. application Ser. No. 16/310,897 filed Dec. 18, 2018, which is a national stage application filed under 35 U.S.C. § 371 of international application no. PCT/JP2017/022478 filed Jun. 19, 2017, and it claims priority to Japanese patent application no. 2016-121453 filed Jun. 20, 2016.

TECHNICAL FIELD

The present invention relates to a process for preparing substituted polycyclic pyridone derivatives and crystals thereof. Specifically, the present invention relates a process for preparing substituted polycyclic pyridone derivatives having cap-dependent endonuclease inhibitory activity and intermediates thereof.

BACKGROUND ART

WO2010/110409 (Patent Document 1) discloses a process for preparing a polycyclic pyridone derivative using a pyrone derivative and a pyridone derivative (Example 3).

[Chem. 1]

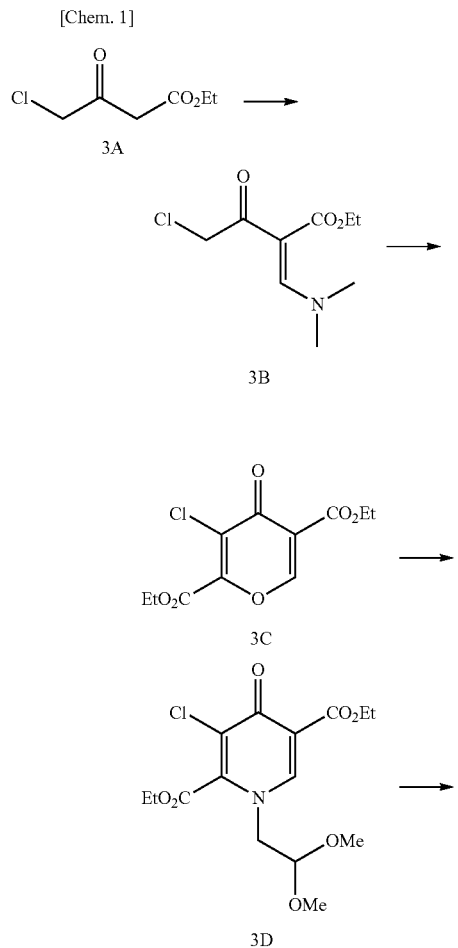

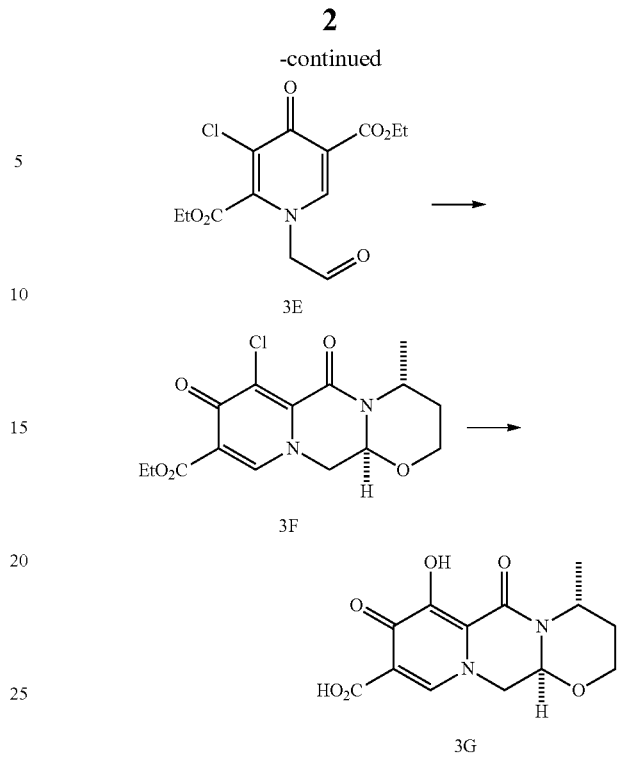

WO2010/147068 (Patent Document 2) and WO2012/039414 (Patent Document 3) disclose a process using a pyridone derivative for the preparation of a polycyclic pyridone derivative (Example 165).

[Chem. 2]

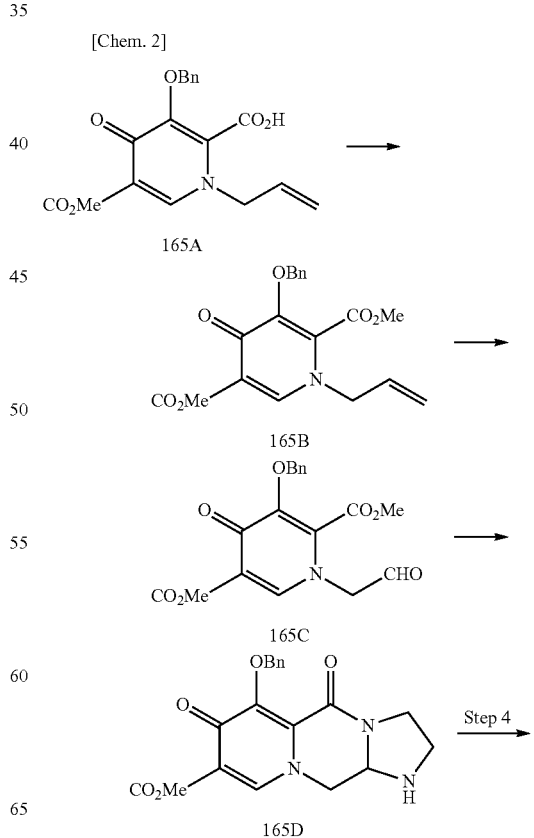

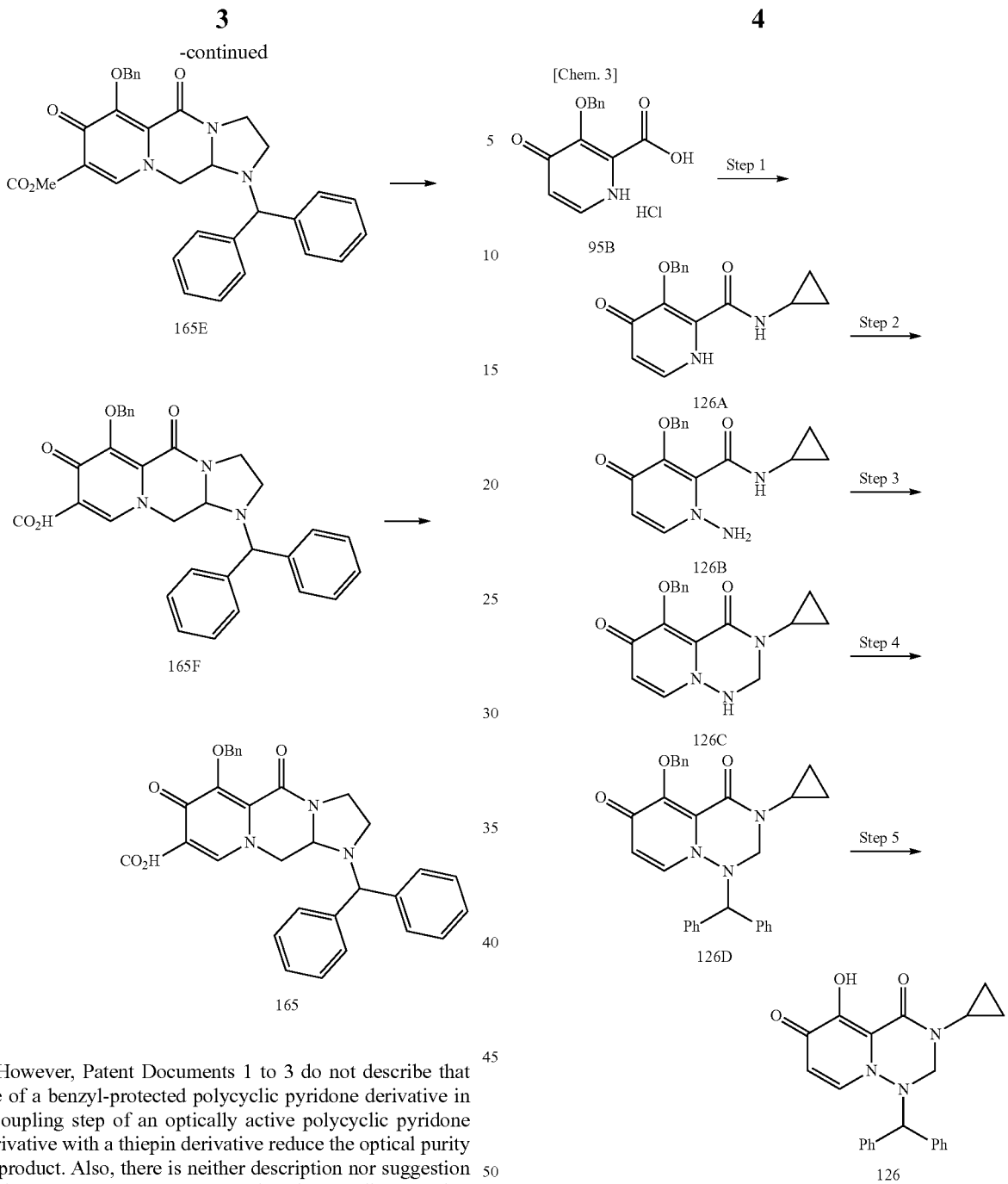

However, Patent Documents 1 to 3 do not describe that use of a benzyl-protected polycyclic pyridone derivative in a coupling step of an optically active polycyclic pyridone derivative with a thiepin derivative reduce the optical purity of product. Also, there is neither description nor suggestion in the Patent Documents 1 to 3 that the coupling reaction proceeds in good yield without reduction in optical purity when the coupling reaction is carried out using a hexyl-protected polycyclic pyridone derivative. Furthermore, there is neither description nor suggestion that the reaction proceeds in high yield without reduction in optical purity when the reaction is carried out in the presence of a magnesium salt in the reaction to exchange the protecting group in the polycyclic pyridone derivative from a protecting group other than unsubstituted alkyl to unsubstituted alkyl.

Patent Document 1 discloses the following process comprising a step of coupling a benzyl-protected polycyclic pyridone derivative with a benzhydryl derivative (Example 21). However, there is neither description nor suggestion of any step to exchange the protective group in the polycyclic pyridone derivative.

Patent Document 2 discloses a step of coupling a substituted tricyclic pyridone derivative with a benzhydryl derivative (Example 175). However, there is neither description nor suggestion of any step to exchange the protective group in the tricyclic pyridone derivative.

[Chem. 4]

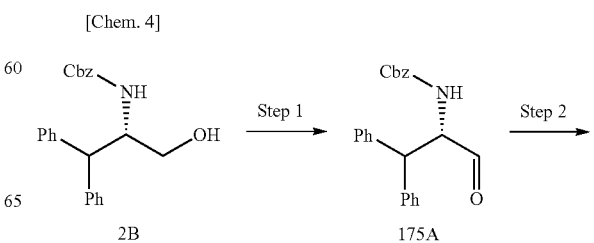

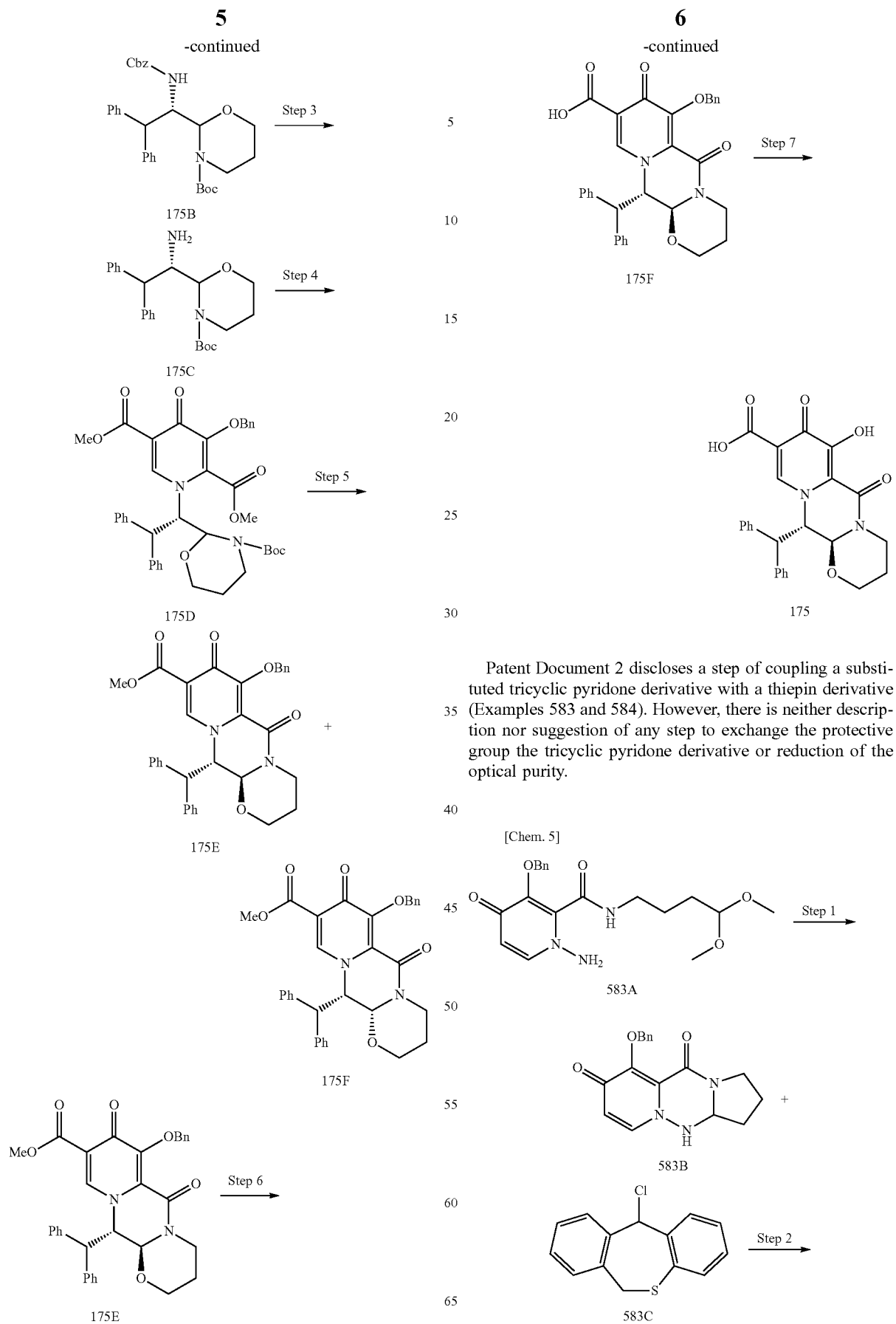
Patent Document 2 discloses a step of coupling a substituted tricyclic pyridone derivative with a thiepin derivative (Examples 583 and 584). However, there is neither description nor suggestion of any step to exchange the protective group the tricyclic pyridone derivative or reduction of the optical purity.
[Chem. 5]

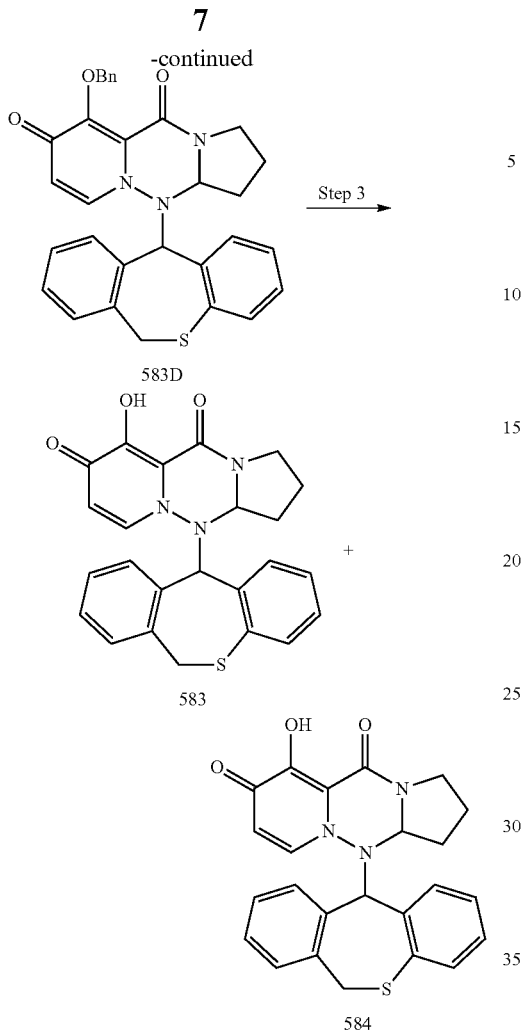

583D

583

584

PRIOR ART DOCUMENTS

Patent Documents

WO2010/110409
WO2010/147068
WO2012/039414

SUMMARY

Technical Problem

PCT/JP2016/63139 describes that the compound, which is the compound of formula (V) or (VI) as disclosed herein, has a cap-dependent endonuclease inhibitory activity and is useful as a therapeutic and/or prophylactic agent for symptoms and/or diseases caused by infection of influenza virus.

One object of the present invention is to provide a novel and useful process for the preparation of substituted polycyclic pyridone derivatives of formula (V) or (VI) having cap-dependent endonuclease inhibitory activity and intermediates thereof of formula (II) or (IV).

Solution to Problem

The present inventors have found a reduction in the optical purity of an optically active substituted cyclic pyridone derivative occurs in a coupling step of an optically active substituted tricyclic pyridone derivative with a thiepin derivative.

The present inventors also have found a process to achieve a coupling reaction of an optically active substituted tricyclic pyridone derivative with a thiepin derivative without causing a reduction of the optical purity, by exchanging from a protective group other than unsubstituted alkyl, such as benzyl group, to hexyl group.

The present invention relates to the following.

(1) A process for preparing a compound of the formula (II):

[Chem. 6]

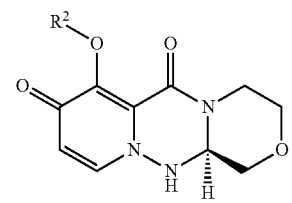

wherein $R^2$ is unsubstituted alkyl,
characterized by reacting a compound of the formula (I):

[Chem. 7]

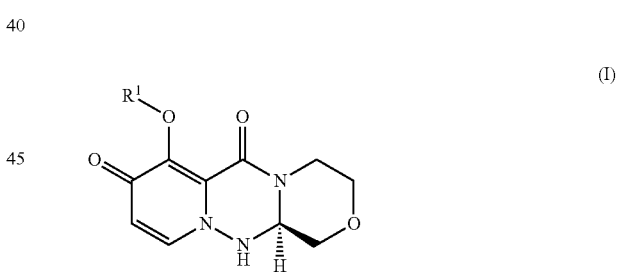

wherein $R^1$ is hydrogen or a protecting group other than unsubstituted alkyl,
with a compound of the formula: $R^2$—OH, wherein $R^2$ is as defined above, in the presence of a sodium salt and/or a magnesium salt.

(2) The process according to (1) wherein the reaction is carried out in the presence of a magnesium salt.

(3) The process according to (1), wherein the reaction is carried out in the presence of isopropyl magnesium chloride.

(4) The process according to any one of (1) to (3) wherein $R^1$ is benzyl.

(5) The process according to any one of (1) to (4) wherein $R^2$ is hexyl.

(6) A process for preparing a compound of the formula (IV):

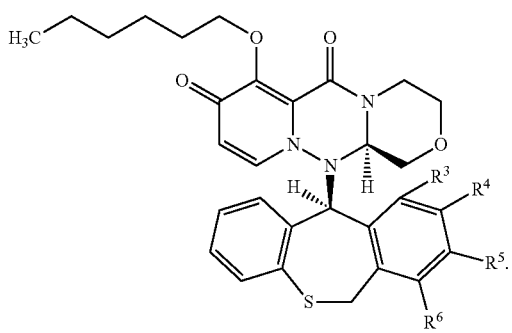

wherein $R^3$, $R^4$, $R^5$ and $R^6$ are each independently hydrogen or halogen, provided that one or two of $R^3$, $R^4$, $R^5$ and $R^6$ is halogen,
characterized by reacting a compound of the formula (II'):

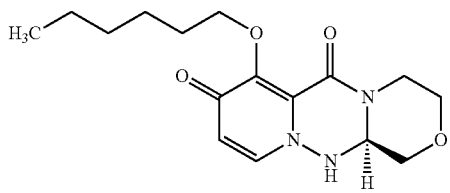

with a compound of the formula (III):

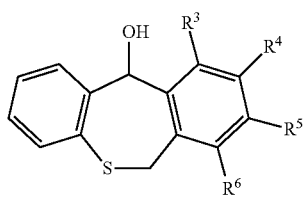

wherein $R^3$, $R^4$, $R^5$ and $R^6$ are as defined above.
(7) The process according to (6) wherein $R^3$ is hydrogen, $R^4$ is hydrogen, $R^5$ is fluorine, and $R^6$ is fluorine.

(8) A process for preparing the compound of the formula (V) or formula (VI):

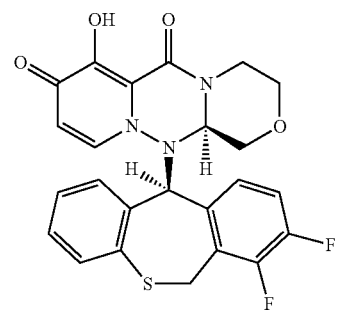

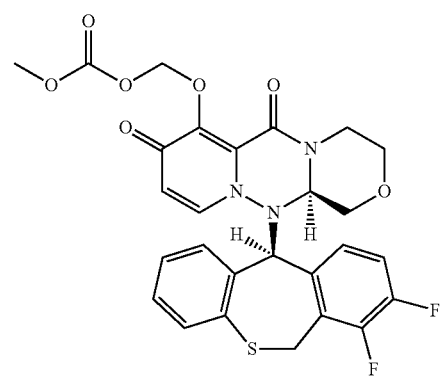

which comprises the process according to any one of (1) to (7).
(9) A compound of the formula (II'):

[Chem. 12]

(II')

$H_3C$ or a salt thereof.
(10) The salt of the compound according to (9) which is a tosylate.
(11) A crystal of the salt according to (10).
(12) The crystal according to (11) characterized by an X-ray powder diffraction pattern wherein the diffraction angles (2θ) of at least two peaks are selected from the group consisting of 5.9±0.2°, 8.4±0.2°, 11.6±0.2°, 12.7±0.2°, 13.1±0.2° and 15.7±0.2°.
(13) The crystal according to (11) characterized by an X-ray powder diffraction pattern comprising peaks at the diffraction angles (2θ) of 5.9±0.2°, 8.4±0.2°, 11.6±0.2°, 12.7 0.2°, 13.1±0.2° and 15.7±0.2°.
(14) The crystal according to (11) characterized by a powder X-ray diffraction spectrum substantially identical with FIG. 4.

(15) A compound of the formula (IV'):

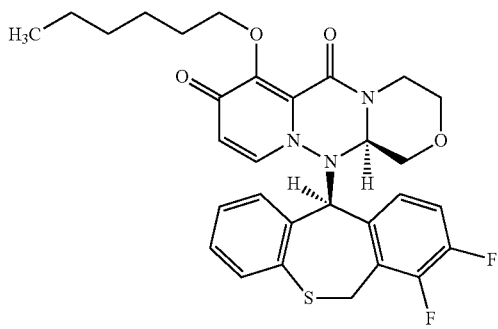

or a salt thereof.
(16) The salt of the compound according to (15) which is a mesylate.
(17) A crystal of the salt according to (16).
(18) The crystal according to (17) characterized by an X-ray powder diffraction pattern wherein the diffraction angles (2θ) of at least two peaks are selected from the group consisting of 7.1±0.2°, 9.3±0.2°, 12.6±0.2°, 14.1±0.2°, 17.7±0.2°, 18.7±0.2°, 19.2±0.2°, 22.2±0.2°, 25.4±0.2°, 27.7±0.2°, 28.5±0.2°, and 37.8±0.2°.
(19) The crystal according to (17) characterized by an X-ray powder diffraction pattern comprising peaks at the diffraction angles (2θ) of 7.1±0.2°, 9.3±0.2°, 12.6±0.2°, 14.1±0.2°, 17.7±0.2°, 18.7±0.2°, 19.2±0.2°, 22.2±0.2°, 25.4±0.2°, 27.7±0.2°, 28.5±0.2°, and 37.8±0.2°.
(20) The crystal according to (17) having the melting point of 219° C.±2° C. in differential scanning calorimetry.
(21) The crystal according to (17) characterized by a powder X-ray diffraction spectrum substantially identical with FIG. 5.
(22) A compound of the formula (VII):

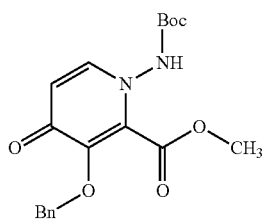

or a salt thereof.
(23) A monohydrate of the compound according to (22).
(24) The monohydrate according to (23) characterized by an X-ray powder diffraction pattern wherein the diffraction angles (2θ) of at least two peaks are selected from the group consisting of 5.4±0.2°, 7.5±0.2°, 8.4±0.2°, 10.6±0.2°, 11.9±0.2°, 13.5±0.2°, 20.2±0.2° and 22.9±0.2°.
(25) The monohydrate according to (23) characterized by an X-ray powder diffraction pattern comprising peaks at the diffraction angles (2θ) of 5.4±0.2°, 7.5±0.2°, 8.4±0.2°, 10.6±0.2°, 11.9±0.2°, 13.5±0.2°, 20.2±0.2° and 22.9±0.2°.
(26) The monohydrate according to (23) characterized by a powder X-ray diffraction spectrum substantially identical with FIG. 1.
(27) A solvate of the compound of the formula (VIII):

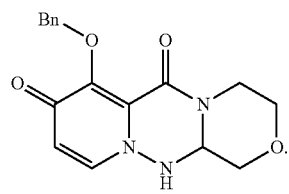

(28) A ½ hydrate of the compound of the formula (VIII).
(29) The ½ hydrate according to (28) characterized by an X-ray powder diffraction pattern wherein the diffraction angles (2θ) of at least two peaks are selected from the group consisting of 9.5±0.2°, 13.4±0.2°, 18.0±0.2°, 19.3±0.2°, 21.2±0.2°, 22.5±0.2°, 22.8±0.2°, 23.6±0.2°, 27.5±0.2°, and 28.1±0.2°.
(30) The ½ hydrate according to (28) characterized by an X-ray powder diffraction pattern comprising peaks at the diffraction angles (2θ) of 9.5±0.2°, 13.4±0.2°, 18.0±0.2°, 19.3±0.2°, 21.2±0.2°, 22.5±0.2°, 22.8±0.2°, 23.6±0.2°, 27.5±0.2°, and 28.1±0.2°.
(31) The ½ hydrate according to (28) characterized by a powder X-ray diffraction spectrum substantially identical with FIG. 2.
(32) A compound of the formula (IX):

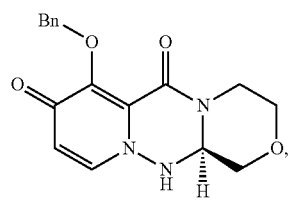

a salt thereof or a solvate thereof.
(33) A crystal of a compound of the formula (IX).
(34) The crystal according to (33) characterized by an X-ray powder diffraction pattern wherein the diffraction angles (2θ) of at least two peaks are selected from the group consisting of 7.1±0.2°, 14.1±0.2°, 15.1±0.2°, 21.0±0.2°, 21.2±0.2°, 22.9±0.2°, and 23.4±0.2°.
(35) The crystal according to (33) characterized by an X-ray powder diffraction pattern comprising peaks at the diffraction angles (2θ) of 7.1±0.2°, 14.1±0.2°, 15.1±0.2°, 21.0±0.2°, 21.2±0.2°, 22.9±0.2°, and 23.4±0.2°.
(36) The crystal according to (33) characterized by a powder X-ray diffraction spectrum substantially identical with FIG. 3.

(37) A crystal of the compound of the formula (V):

[Chem. 17]

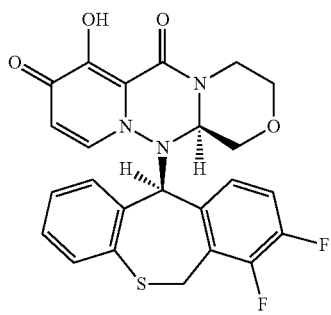

(V)

or a crystal of a pharmaceutically acceptable salt thereof.
(38) The crystal according to (37) characterized by an X-ray powder diffraction pattern wherein the diffraction angles (2θ) of at least two peaks are selected from the group consisting of 9.6±0.2°, 10.9±0.2°, 17.8±0.2°, 21.5±0.2°, 22.1±0.2°, 23.5±0.2°, and 24.8±0.2°.
(39) The crystal of the compound according to (37) characterized by an X-ray powder diffraction pattern comprising peaks at the diffraction angles (2θ) of 9.6±0.2°, 10.9±0.2°, 17.8±0.2°, 21.5±0.2°, 22.1±0.2°, 23.5±0.2° and 24.8±0.2°.
(40) The crystal of the compound according to (37) characterized by a powder X-ray diffraction spectrum substantially identical with FIG. 6.

According to the process of the present invention, a polycyclic pyridone derivative of the formula (V) or (VI) can be efficiently prepared with high optical purity.

DETAILED DESCRIPTION OF THE PREFERRED EMBODIMENTS

Figure 1:
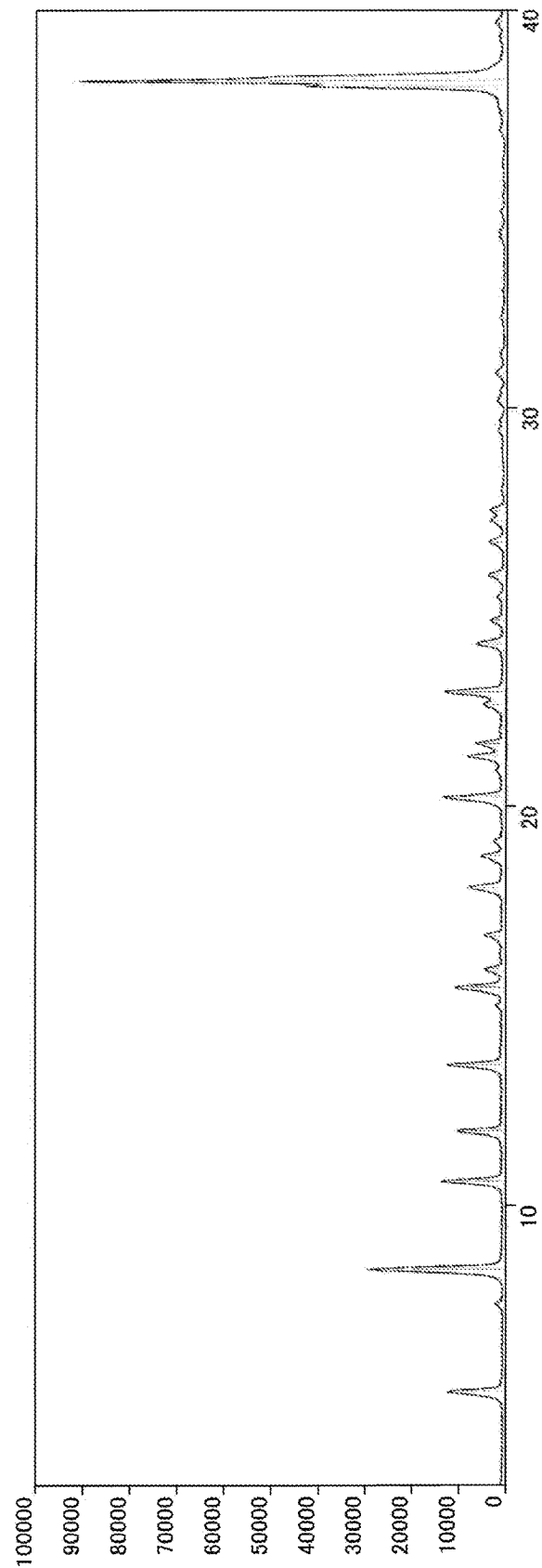
FIG. 1 is a powder X-ray diffraction pattern of Compound 3.

The meanings of the terms as used herein are explained below. Unless otherwise specified, each term has the same meaning when used alone or in combination with other terms.

The term "consisting of" means to have only the described elements.
The term "comprising" means not to limit to the described elements and not to exclude undescribed elements.
"Halogen" includes fluorine, chlorine, bromine or iodine. Fluorine and chlorine are preferable, and fluorine is particularly preferable.
"Alkyl" means a C1 to C6 straight or branched alkyl, and includes C1 to C4 alkyl, C1 to C3 alkyl and the like. Examples include methyl, ethyl, n-propyl, isopropyl, n-butyl, isobutyl, sec-butyl, tert-butyl, n-pentyl, isopentyl, neopentyl, hexyl, isohexyl and the like.
Example of the protecting group other than unsubstituted alkyl of $R^1$ includes benzyl.
Example of the unsubstituted alkyl of $R^2$ includes methyl, ethyl, n-propyl, isopropyl, n-butyl, isobutyl, sec-butyl, tert-butyl, n-pentyl, isopentyl, neopentyl, hexyl, and isohexyl; and n-propyl, isobutyl, hexyl and the like are preferable; and hexyl is particularly preferable.
"Protecting group other than unsubstituted alkyl" is not limited so long as it is a protecting group other than the above "alkyl" and it is removed in the presence of sodium salt and/or magnesium salt. Example includes substituted alkyl and the like, preferably benzyl and the like.
"Sodium salt" is not limited so long as it is able to remove "protecting group other than alkyl". Examples include sodium hydroxide, sodium hydride, sodium isopropyl oxide, sodium tert-pentoxide, isopropyl magnesium chloride and the like. Preferred are sodium tert-pentoxide and isopropyl magnesium chloride, and isopropyl magnesium chloride is particularly preferable.
Preferred embodiments of $R^1$, $R^2$, $R^3$, $R^4$, $R^5$, $R^6$ and "sodium salt and/or magnesium salt" are described below. Compounds having a possible combination of the following embodiments are preferable.
$R^1$ includes hydrogen or a protecting group other than unsubstituted alkyl. In a preferred embodiment, $R^1$ is a protecting group other than unsubstituted alkyl, and benzyl is particularly preferable.
$R^2$ includes unsubstituted alkyl. In a preferred embodiment, $R^2$ includes methyl, ethyl, n-propyl, isopropyl, n-butyl, isobutyl, sec-butyl, tert-butyl, n-pentyl, isopentyl, neopentyl, hexyl, isohexyl and the like, and n-propyl, isobutyl, hexyl and the like are preferable, and hexyl is particularly preferable.
In a preferred embodiment, "sodium salt and/or magnesium salt" is preferably "magnesium salt", and isopropyl magnesium chloride, cyclohexyl magnesium chloride and the like are more preferable, and isopropyl magnesium chloride is particularly preferable.
$R^3$, $R^4$, $R^5$ and $R^6$ are each independently hydrogen or halogen, and the number of halogen in $R^3$, $R^4$, $R^5$ and $R^6$ is one or two.
In a preferred embodiment, $R^3$ is hydrogen.
In a preferred embodiment, $R^4$ is hydrogen.
In a preferred embodiment, $R^5$ is fluorine.
In a preferred embodiment, $R^6$ is fluorine.
The term "the number of halogen in $R^3$, $R^4$, $R^5$ and $R^6$ is one or two", as used herein, means that one or two of $R^3$, $R^4$, $R^5$ and $R^6$ is halogen.
In the present description, reacting a compound with a compound includes reacting a salt of such compound or a solvate thereof.
Examples of the pharmaceutically acceptable salt of the compound of the present invention include salts with alkaline metals (e.g., lithium, sodium, potassium, etc.), alkaline earth metals (e.g., calcium, barium, etc.), magnesium, transition metals (e.g., zinc, iron, etc.), ammonia, organic bases (e.g., trimethylamine, triethylamine, dicyclohexylamine, ethanolamine, diethanolamine, triethanolamine, meglumine, ethylenediamine, pyridine, picoline, quinolin, etc.) or amino acids, or salts with inorganic acids (e.g., hydrochloric acid, sulfuric acid, nitric acid, carbonic acid, hydrobromic acid, phosphoric acid, hydroiodic acid, etc.), or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid, etc.), particularly, salts with hydrochloric acid, sulfuric acid, phosphoric acid, tartaric acid, methanesulfonic acid and the like. These salts can be formed in accordance with the conventional methods.

Examples of the pharmaceutically acceptable salt of the compound of formula (V) include salts with alkaline metals (e.g., lithium, sodium, potassium, etc.), alkaline earth metals (e.g., calcium, barium, etc.), magnesium, transition metals (e.g., zinc, iron, etc.), and salts with alkaline metals (e.g., lithium, sodium, potassium, etc.) and salts with alkaline earth metals (e.g., calcium, barium, etc.) are preferable.

The compound of the present invention or a pharmaceutically acceptable salt thereof may form a solvate, such as hydrate, and/or a crystalline polymorph, and the present invention includes such various solvates as well as crystalline polymorphs. "Solvates" may be those wherein any numbers of solvent molecules (e.g., water molecules or the like) are coordinated with the compound of present the invention. When the compound of the present invention or a pharmaceutically acceptable salt thereof is allowed to stand in the atmosphere, it may absorb water, resulting in attachment of adsorbed water or formation of hydrates. In addition, the compound of the present invention or a pharmaceutically acceptable salt thereof may be recrystallized to form a crystal polymorphism.

A method for characterizing the crystal of the present invention is illustrated below. Unless otherwise mentioned, the numerical values in the description and claims are approximate values. The numerical values may vary due to instrument calibration, instrument error, material purity, crystal size, sample size, and other factors.

The term "crystal" as used herein means a material having an ordered long-range molecular structure. The degree of crystallinity of the crystalline form can be measured by a number of techniques including, for example, powder X-ray diffraction, moisture adsorption, differential analysis, calorimetric analysis, solution colorimetry, dissolution properties.

In general, a crystalline organic compound is composed of a large number of atoms periodically arranged in a three-dimensional space. The structural periodicity normally manifests distinct physical properties that are clearly distinguishable by most spectroscopic probes (e.g., X-ray diffraction, infrared spectra, Raman spectra and solid state NMR).

Among others, X-ray powder diffraction (XRPD) is acknowledged to be one of the most sensitive methods to determine the crystallinity of solids. X-rays which are irradiated to crystals are reflected by the crystal lattice planes and mutually interfere. Then, only the diffraction lines in the direction which fulfill the conditions predicted by Bragg's law are intensified, and the intensity of the order diffraction lines are canceled and not observed. On the other hand, in the case of amorphous solids, the ordered diffraction lines over a long-range are not observed. Amorphous solids usually exhibit a broad XRPD pattern called halo pattern because of the absence of the long range order of repeating crystal lattice.

A crystalline form of the polycyclic pyridone derivatives, intermediates, salts thereof and/or solvates thereof disclosed in this description preferably has a distinguishable X-ray powder diffraction profile. For example, a crystalline form of the compound of formula (V) can be preferably distinguished by the presence of characteristic diffraction peaks. The characteristic diffraction peaks as used herein are those selected from an observed diffraction pattern. Preferably, the characteristic diffraction peaks are selected from the diffraction pattern among approximately twenty peaks, more preferably approximately ten peaks, and most preferably approximately five peaks.

In general, it is known that the relative intensities of various peaks in the Tables and Figures as shown below may vary due to a number of factors, such as the orientation effects of crystals on the X-ray beam, the purity of the material to be analyzed or the degree of crystallinity of the sample. The peak positions may also shift for variations in the sample height. Furthermore, a measurement using a different wavelength will result in a different shift according to the Bragg equation ($n\lambda = 2d \sin \theta$). Such XPRD patterns obtained by using a different wavelength are within the scope of the present invention.

The crystalline form of the present invention can be characterized by means of thermal analysis.

DSC (Differential Scanning Calorimetry)

DSC is one of principal measuring methods for thermal analysis and a method of measuring the thermal properties of the substance as an aggregate of atoms/molecules. A differential scanning calorimetry curve can be obtained by measuring change of heat capacity over temperature or time of a pharmaceutical active ingredient by DSC, and plotting the obtained data to temperatures or times. The information of the onset temperature, endothermic maximum and enthalpy of melting a pharmaceutical active ingredient can be obtained from a differential scanning calorimetry curve.

(Preparation of Compound of the Present Invention)

A general method for preparation of the compound of the present invention is exemplified below. Further, extraction, purification and the like may be carried out by conventional methods practiced in organic chemistry experiments.

The synthesis of the compound of the present invention can be carried out with reference to methods known in the art.

As a raw material compound, commercially available compounds, compounds described in the present description, compounds described in the references cited in the present description, and other known compounds can be utilized.

If a salt of the compound of the present invention is desired, it may be purified as it is in the case where the compound of the present invention is obtained in the form of a salt. In case where the compound is obtained in a free form, it is dissolved or suspended in a suitable organic solvent and added with an acid or a base to form a salt by an ordinary method.

In addition, the compound of the present invention and a pharmaceutically acceptable salt thereof may exist in a form of adduct with water or various solvents (hydrate or solvate). The present invention also include such adducts.

The wedge and dotted-lines indicate absolute configuration.

The process of the present invention can be carried out, for example, as follows.

Step 1

[Chem. 18]

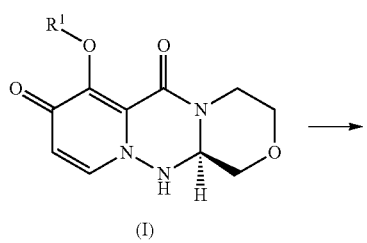

(I)

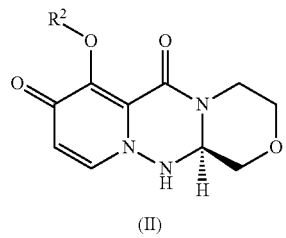

(II)

wherein $R^1$ is hydrogen or a protecting group other than unsubstituted alkyl and $R^2$ is unsubstituted alkyl.

In this step, a compound of the formula (I) is reacted with an alcohol of the formula: $R^2$—OH in the presence of a sodium salt and/or a magnesium salt to give a compound of the formula (II).

The solvent is not limited so long as it allows the above process to proceed efficiently. Examples of such solvent include dichloromethane, toluene, tetrahydrofuran and the like, which may be used alone or in combination. The reaction can be carried out in a single of mixed solvent, or without solvent. Preferred solvent is tetrahydrofuran.

Examples of the sodium salt and/or magnesium salt include sodium hydroxide, sodium hydride, sodium isopropoxide, sodium tert-pentoxide, isopropyl magnesium chloride, cyclohexyl magnesium chloride and the like. Preferred is isopropyl magnesium chloride. The salt may be used in an amount of 0.1 to 5 molar equivalents, preferably 0.3 to 0.5 molar equivalents, to the compound (I).

The reaction temperature is not limited, but the reaction usually can be conducted at about 0 to 100° C., preferably at 0° C. to room temperature.

The reaction time is not limited, but the reaction usually can be conducted for 0.5 hour to 24 hours, preferably for 1 to 10 hours.

Step 2

[Chem. 19]

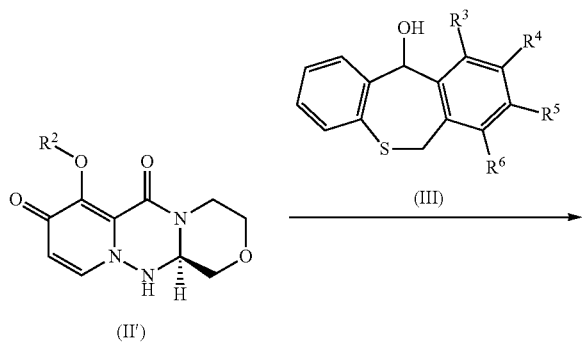

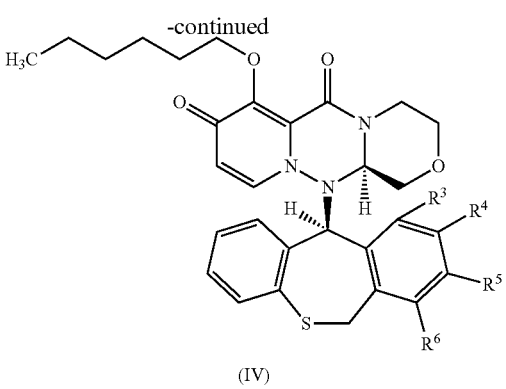

(IV)

wherein $R^3$, $R^4$, $R^5$ and $R^6$ are each independently hydrogen or halogen provided that one or two of $R^3$, $R^4$, $R^5$ and $R^6$ is halogen. Other symbols are as defined above.

In this step, a compound of the formula (II') is reacted with a compound of the formula (III) in the presence of a condensing agent to obtain a compound of the formula (IV).

The solvent is not limited so long as it allows the above step to proceed efficiently. Example of the solvent include ethyl acetate, cyclohexane, isopropyl acetate, propyl acetate, toluene, 1,4-dioxane, DMA, DMF, toluene, heptane, cyclopentyl methyl ether and the like, which may be used alone or in combination. The reaction can be carried out in a single of mixed solvent, or without solvent. Preferred solvent is a mixed solvent of ethyl acetate and cyclohexane.

Examples of the condensing agent include propylphosphonic anhydride, methanesulfonic acid, trifluoroacetic acid, p-toluenesulfonic acid monohydrate, 10-camphorsulfonic acid, concentrated sulfuric acid, dichloroacetic acid, tetramethylammonium hydrogen sulfate and the like, and they can be used alone or in combination, preferably, a mixture of propylphosphonic anhydride and methanesulfonic acid. The condensing agent may be used in an amount of 1 to 5 molar equivalents, preferably 1 to 3 molar equivalents, to the compound (II').

The reaction temperature is not particularly limited, but the reaction usually can be conducted at about 0 to 100° C., preferably at 0° C. to room temperature.

The reaction time is not limited, but the reaction usually can be conducted for 0.5 hour to 24 hours, preferably for 1 to 10 hours.

Step 3

[Chem. 20]

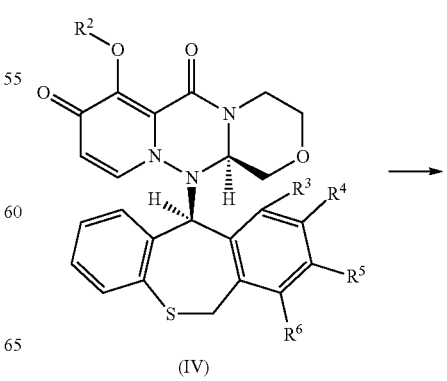

(IV)

-continued

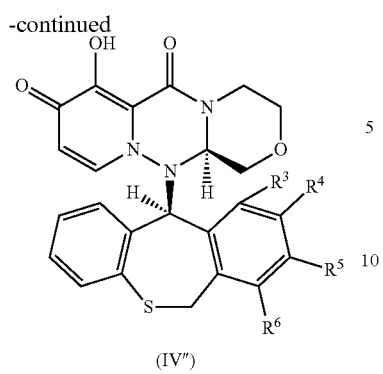
(IV")

wherein the variables are as defined above.

In this step, a compound of the formula (IV) is reacted with a metal salt to obtain a compound of the formula (IV").

The solvent is not limited so long as it allows the above process to proceed efficiently. Examples of such solvent include N-methylpyrrolidone, N,N-dimethylformamide, N,N-dimethylacetamide and the like, which may be used alone or in combination. N-methylpyrrolidone is preferable.

Examples of the metal salt include lithium chloride and lithium bromide and the like, and lithium chloride is preferable. The metal salt may be used in an amount of 1 to 20 molar equivalents, preferably 5 to 10 molar equivalents, to the compound (IV).

The reaction temperature is not particularly limited, but the reaction usually can be conducted at about 0 to 100° C., preferably at room temperature to 100° C.

The reaction time is not limited, but the reaction usually can be conducted for 0.5 hour to 48 hours, preferably for 12 to 24 hours.

Step 4

[Chem. 21]

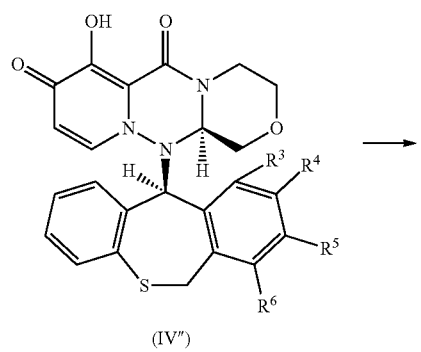
(IV")

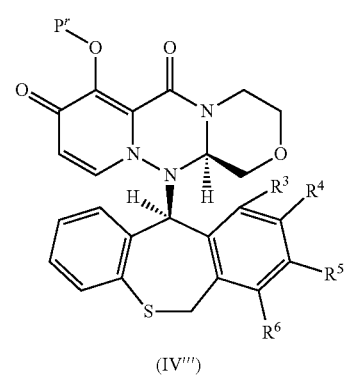
(IV''')

wherein P$^r$ is a protecting group for a hydroxy group such as an ester group or an ether group, and the other variables are as defined above.

In this step, compound (V''') can be obtained according to a conventional method for converting the hydroxyl group of compound (IV") to an ester group or an ether group. Examples for such method can be found in Protective Groups in Organic Synthesis, Theodora W Green (John Wiley & Sons), Prog. Med 5: 2157-2161 (1985) and Supplied by The British Library—"The world's Knowledge".

As used herein, "diastereomer ratio" refers to the ratio of the HPLC area percentage between the two stereoisomers shown below.

[Chem. 22]

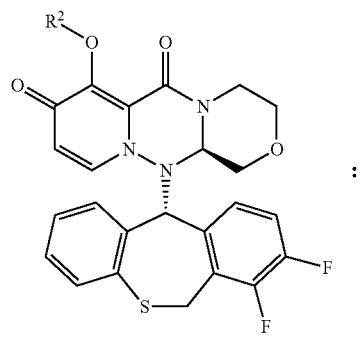
a

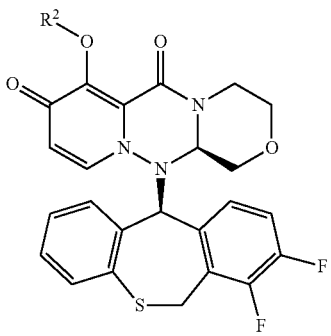
b

The compounds of formula (V) is useful for symptoms and/or diseases induced by influenza viruses. It is useful for the treatment, prevention, and/or symptom relief for example, cold symptom involved with fever, chills, headache, muscle pain, and feeling of generalized worthlessness, airway inflammation such as sore throat, Nasal discharge, congested nose, cough, phlegm, gastrointestinal symptom such as stomachache, emesis, diarrehea, in addition, concomitant disease involved with secondary infection such as acute encephalopathy, pneumonia.

The compound represented by the formula (VI) can be an excellent medicine because it has advantages such as high oral absorbability, good bioavailability, good clearance, high pulmonary migration, and the like.

The compound represented by the formula (V) can be a medicine with reduced side effects because it has high inhibitory activity to cap-dependent endonuclease, which is a virus-specific enzyme, and thus it has a highly specific effect.

Furthermore, the compound of the formula (V) and/or the compound of the formula (VI) are excellent in terms of metabolic stability, high solubility, high oral absorbability, good bioavailability, good clearance, high lung transitivity, long half-life, high binding rate to non-protein, low hERG channel inhibition, low CYP inhibition, CPE (CytoPathic Effect) suppression effect, and/or in that it also has advantages that it is negative in phototoxicity test, Ames test, genotoxicity test, or has no toxicity such as hepatic injury. Thus, the compound of the formula (V) and/or the compound of the formula (VI) can be an excellent medicament.

The compounds of the formula (V) and/or the compound of the formula (VI) can be administered by oral or parenteral route. For oral administration, the compounds of the formula (V) and/or the compound of the formula (VI) can be used in any form of usual formulations, for example, formulations in a solid form such as tablets, powders, granules, capsules; formulations in a liquid form such as aqueous formulation; oily suspension; syrup or elixir. For parenteral administration, the compounds of the formula (V) and/or the compound of the formula (VI) can be used in a form of aqueous or oily suspending injection, or nose drops. In the preparation of such formulation, conventional excipients, binding agents, lubricants, aqueous solvents, oleaginous solvents, emulsifying agents, suspending agents, preservatives, stabilizers, and the like can be optionally used. A pharmaceutical composition comprising the compound of the formula (V) and/or the compound of the formula (VI) may be prepared by combining (for example, blending) a therapeutically effective amount of the compound of the formula (V) and/or the compound of the formula (VI) with a pharmaceutically acceptable carrier or diluent.

For oral administration, daily dosage of the compound of the formula (V) and/or the compound of the formula (VI) can be approximately 0.05-3000 mg, preferably approximately 0.1-1000 mg per day for an adult, while such dosage varies depending on the administration route therefor, age, body weight, conditions of the patient, and disease in the patient. The dosage may be divided for administration, if necessary. In case of parenteral administration, the daily dosage for an adult can be between approximately 0.01-1000 mg, preferably approximately 0.05-500 mg.

EXAMPLES

The present invention is explained in more detail with reference to the Examples, Reference Examples, Preparation Examples for intermediates, and Test Examples, but the present invention is not limited to these examples.

The NMR analysis in the Reference Examples and Examples were conducted using DMSO-d6, CDCl$_3$ at 400 MHz.

Powder X-Ray Diffraction Pattern

Powder X-ray diffraction analysis of the crystal obtained in each Example was conducted according to powder X-ray diffraction analysis method in General Tests in Japanese Pharmacopoeia under the following conditions.

(Device)
MinFlex600 RINT-TTRIII (Rigaku)
(Method)
Detector: High-speed one-dimensional detector (D/TecUltra 2) and variable knife edge
Measurement method: reflection method
Type of light source: Cu bulb
Working wavelength: CuKα ray
Tube current: 10 mA, or 15 mA
Tube voltage: 30 Kv, or 40 Kv
Sample plate: aluminum or glass
X-ray incident angle (θ): 3-40°, sampling width: 0.01°, or
X-ray incident angle (θ): 4-40°, sampling width: 0.02°

In general, since diffraction angles (2θ) in powder X-ray diffraction may involve errors within ±0.2°, the values of the diffraction angle include values within the range of about ±0.2°. Therefore, the present invention includes not only crystals in which the diffraction angles of peaks in powder X-ray diffraction completely match but also crystals in which diffraction angles of peaks coincide with errors of about ±0.2°.

(Measurement of Water Content by Karl Fischer Method)

Water content was determined according to General Tests for water determination (coulometric titration) in Japanese Pharmacopoeia. Aquamicron™ AX (Mitsubishi Chemical Corporation) was used as an anolyte solution, and Aquamicron™ CXU was used as a catholyte solution.

In general, a water content measurement by Karl Fischer Method may involve an error within the range of ±0.3%. Accordingly, a specific value of water content as measured should embrace any value within the range of ±0.3%.

TG/DTA Measurement

TG/DTA measurement of the crystals obtained in each example was conducted. A sample was weighed in an aluminum pan and measured in an open system. The measurement conditions are shown below.

Apparatus: TG/DTA 7200 (Hitachi High-Tech Science)

Measurement temperature range: 30° C.-250° C.

Heating rate: 10° C./min

In general, TG/DTA measurement may involve an error within the range of ±2° C. Accordingly, a specific value as measured should embrace any value within the range of ±2° C.

Dynamic Vapor Sorption (DVS)

Dynamic vapor sorption analysis of the crystals obtained in each example was conducted. A sample was weighed in a sample pan and measured under the conditions as follows.

Apparatus: DVS Advantage (Surface Measurement Systems Ltd.)

Measurement point: from 0% RH to 95% RH stepped 5%, then 95% RH to 0% RH stepped 5%

Temperature: 25° C. or 60° C.

Measurement of Differential Scanning Calorimetry (DSC)

DSC measurement of the crystals obtained in each example was conducted. A sample was weighed in a stainless steel pan with hermetic seal and measured under the following conditions.

Apparatus: METTLER TOLEDO DSC 822e

Measurement temperature range: 30° C.-300° C.

Heating rate: 10° C./min

Atmosphere: N2 40 mL/min

In general, differential scanning calorimetry (DSC) may involve an error within the range of ±2° C. Accordingly, a specific value as measured by differential scanning calorimetry (DSC) should embrace any value within the range of ±2° C.

The meaning of each term in Examples is as follows.

DMA: N,N-dimethylacetamide

THF: tetrahydrofuran

T3P: propylphosphonic anhydride (cyclic trimer)

Example 1: Preparation of Compound 3

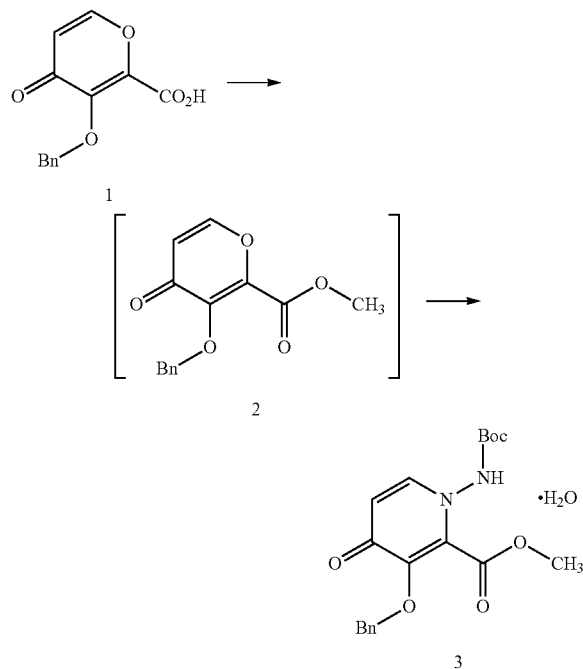

Step 1: Compound 3

DMA (300 mL) was added to Compound 1 (100.00 g, 406 mmol) and the mixture was stirred. Sodium hydrogencarbonate (44.41 g, 529 mmol), dimethyl sulfate (58.91 g, 467 mmol) and DMA (100 mL) were added and stirred at 25° C. for 7 hours. Synthetic hydrochloric acid (16.90 g) and water (500 g) were added to the reaction mixture, and the mixture was extracted twice with ethyl acetate (1000 and 550 mL). The organic layer was washed with 5% brine (300 g) and water (300 g). The combined organic layer was concentrated to about 500 g under reduced pressure. Ethyl acetate (350 mL) was added to the concentrate, and the resulting solution was concentrated to about 500 g under reduced pressure. DMA (300 mL) was added to the concentrate, and the resulting solution was concentrated to about 400 g under reduced pressure. Pyridinium p-toluenesulfonate (265.42 g) and DMA (100 mL) were added to the concentrate and the reaction mixture was heated to 60° C. A solution of tert-butyl carbazinate (69.80 g, 528 mmol) in DMA (100 mL) was added slowly to the reaction mixture over 6 hours. The reaction mixture was stirred at 60° C. for 3 hours and cooled to 25° C. Ethanol (100 mL) and water (290 mL) were added to the reaction mixture, and the reaction mixture was warmed to 30° C. A mixture of ethanol (100 mL) and water (520 mL) was added slowly to the reaction mixture. The reaction mixture was cooled to 0° C. and then stirred at 0° C. for 1.5 hours. The resulting pale yellowish white precipitate was collected by filtration. The resulting solid was washed with a mixture of ethanol (480 mL) and water (720 mL), and dried to give monohydrate of compound 3 (122.70 g, yield 77%) as a pale yellowish white solid.

$^1$H-NMR (400 MHz, CDCl$_3$) δ:1.45 (s, 9H), 3.77 (s, 3H), 5.26 (s, 2H), 6.39 (d, J=7.6 Hz, 1H), 7.27-7.47 (m, 6H), 7.64-8.23 (br s, 1H)

Powder X-ray diffraction 2θ (°): 5.4, 7.5, 8.4, 10.6, 11.9, 13.5, 20.2, 22.9

The powder X-ray diffraction pattern of Compound 3 is shown in FIG. 1.

Water content by Karl Fischer method: 4.5%

Example 2: Preparation of Compound 9

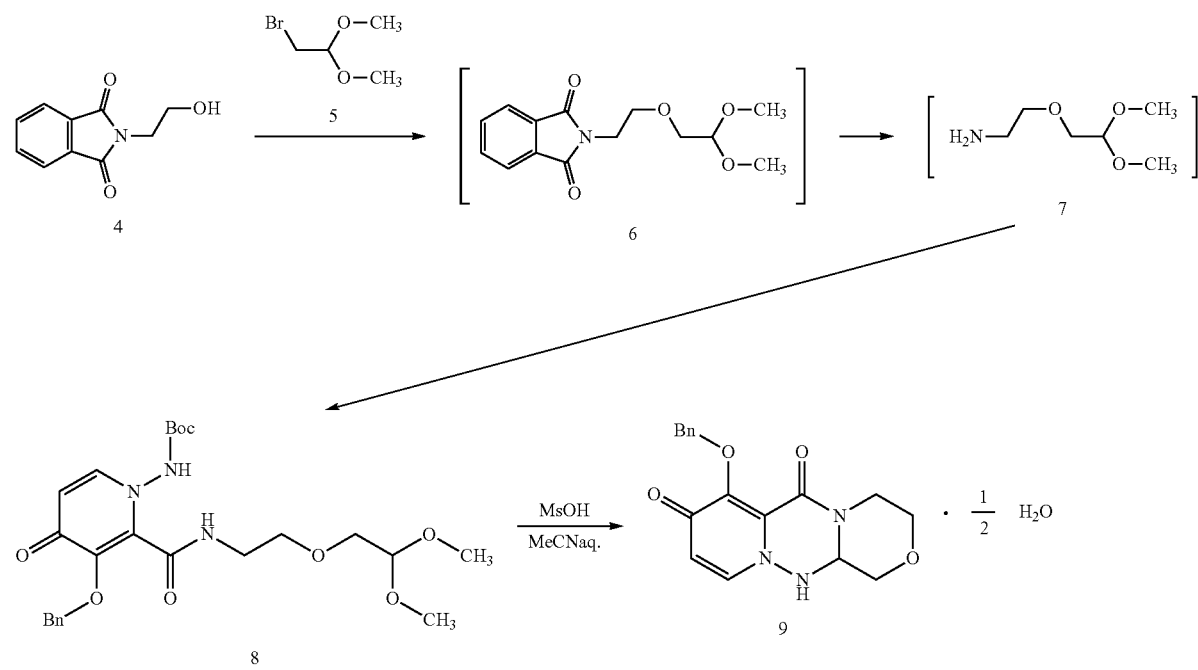

Step 1: Compound 6

Compound 5 (28.29 g, 167.4 mmol) and DMA (65 mL) were added to compound 4 (20.00 g, 104.6 mmol), and the mixture was stirred. After the mixture was warmed to 40° C., sodium tert-butoxide (15.09 g, 157.0 mmol) was added slowly. The reaction mixture was stirred at 40° C. for 3 hours and then cooled to 20° C. Acetic acid (3.14 g) and 10% sodium chloride aqueous solution (64 g) were added to the reaction mixture, and the mixture was extracted twice with ethyl acetate (60 mL). Water (144 mL) was added to the combined organic layer and the mixture was cooled to 0° C. The resulting pale yellowish white precipitate was collected by filtration. The resulting solid was washed with a mixture of methanol (5.4 g) and water (48.6 g), and dried to give Compound 6 (20.44 g, yield 78%) as a pale yellowish white solid.

$^1$H-NMR (CDCl$_3$) δ: 3.34 (s, 6H), 3.53 (d, J=5.2 Hz, 2H), 3.76 (t, J=5.6 Hz, 2H), 3.90 (t, J=5.6 Hz, 2H), 4.43 (t, J=5.2 Hz, 1H), 7.70-7.73 (m, 2H), 7.84-7.87 (m, 2H)

Step 2 Compound 8

Ethanol (20 mL) and water (20 mL) were added to compound 6 (20.02 g, 71.68 mmol), and the mixture was stirred. The mixture was warmed to 60° C. The mixture was added with 60% hydrazine monohydrate aqueous solution (8.99 g, 107.7 mmol) and stirred at 60° C. for 4 hours. After addition of water (40 mL) followed by cooling to 30° C., 17% potassium hydroxide aqueous solution (92.12 g) was added to the reaction mixture. The reaction mixture was extracted four times with methylene chloride (120, 78, 78, 78 mL). The combined organic layer was washed with water (20 mL), and concentrated to about 160 g under reduced pressure. THF (100 mL) was added to the concentrate, and the mixture was concentrated to about 40 g under reduced pressure. THF (100 mL) was added to the concentrate, and the mixture was concentrated to about 40 g under reduced pressure. THF (20 mL) was added to the concentrate, and the mixture was concentrated to about 15 g under reduced pressure to obtain 15 g of a solution of compound 7 in THF.

The above THF solution of compound 7 (14.71 g), THF (7 g) and 1,8-diazabicyclo[5.4.0]-7-undecene (379.0 mg) were added to compound 3 (10.00 g, 25.5 mmol), and the mixture was stirred. The reaction mixture was heated to 60° C. and then stirred at 60° C. for 24 hours. After the reaction mixture was cooled to 25° C., water (28 g) and acetic acid (3.72 g) were added. The reaction mixture was extracted twice with ethyl acetate (50, 30 mL), and the organic layer was washed with 5% sodium hydrogencarbonate aqueous solution (30 g) and water (28 g). The organic layer was concentrated to about 36 g under reduced pressure. Ethyl acetate was added to the reaction mixture, and the resulting mixture was concentrated to about 36 g under reduced pressure. Heptane (65 mL) was added to the concentrate and the mixture was cooled to 5° C. After stirring at 5° C. for 1 hour, the resulting pale yellowish white precipitate was collected by filtration. The resulting solid was washed with a mixture of heptane (32 mL) and ethyl acetate (14 mL), and dried to obtain Compound 8 (10.10 g, yield 81%) as a pale yellowish white solid.

$^1$H-NMR (CDCl$_3$) δ:1.44 (s, 9H), 3.32-3.48 (m, 12H), 4.41 (t, J=5.2 Hz, 1H), 5.29 (s, 2H), 6.38 (d, J=7.6 Hz, 1H), 7.11-7.50 (m, 7H), 8.46 (s, 1H).

Step 3: Compound 9

Acetonitrile (170 mL) and water (30 mL) were added to compound 8 (19.99 g, 40.7 mmol), and the mixture was stirred. The reaction mixture was heated to 60° C., and methanesulfonic acid (11.70 g, 121.7 mmol) was added slowly. The reaction mixture was stirred at 60° C. for 6 hours and then cooled to 25° C. 30% sodium hydroxide aqueous solution (15.91 g) was added to the reaction mixture, and the resulting mixture was concentrated to about 100 g under reduced pressure. Water (50 mL) was added to the concentrate, and the resulting mixture was concentrated to about 100 g under reduced pressure. After stirring the concentrate at 25° C. for 30 minutes, the resulting yellow precipitate was collected by filtration. The obtained solid was washed with water (40 mL) and dried to obtain 0.5 hydrate of Compound 9 (10.43 g, yield 76%) as yellow crystals.

$^1$H NMR (400 MHz, DMSO-d$_6$), δ: 2.95 (ddd, J=13.7, 12.3, 4.3 Hz, 1H), 3.13 (dd, J=11.2, 10.0 Hz, 1H), 3.44 (td, J=11.9, 3.1 Hz, 1H), 3.96-4.08 (m, 2H), 4.14 (dd, J=13.9, 2.4 Hz, 1H), 4.80 (ddd, J=12.6, 9.9, 4.5 Hz, 1H), 5.08 (s, 2H), 6.22 (d, J=7.6 Hz, 1H), 7.24-7.41 (m, 4H), 7.52-7.60 (m, 2H), 7.69 (d, J=7.6 Hz, 1H)

Powder X-ray diffraction 2θ (°): 9.5, 13.4, 18.0, 19.3, 21.2, 22.5, 22.8, 23.6, 27.5, 28.1

Figure 2:
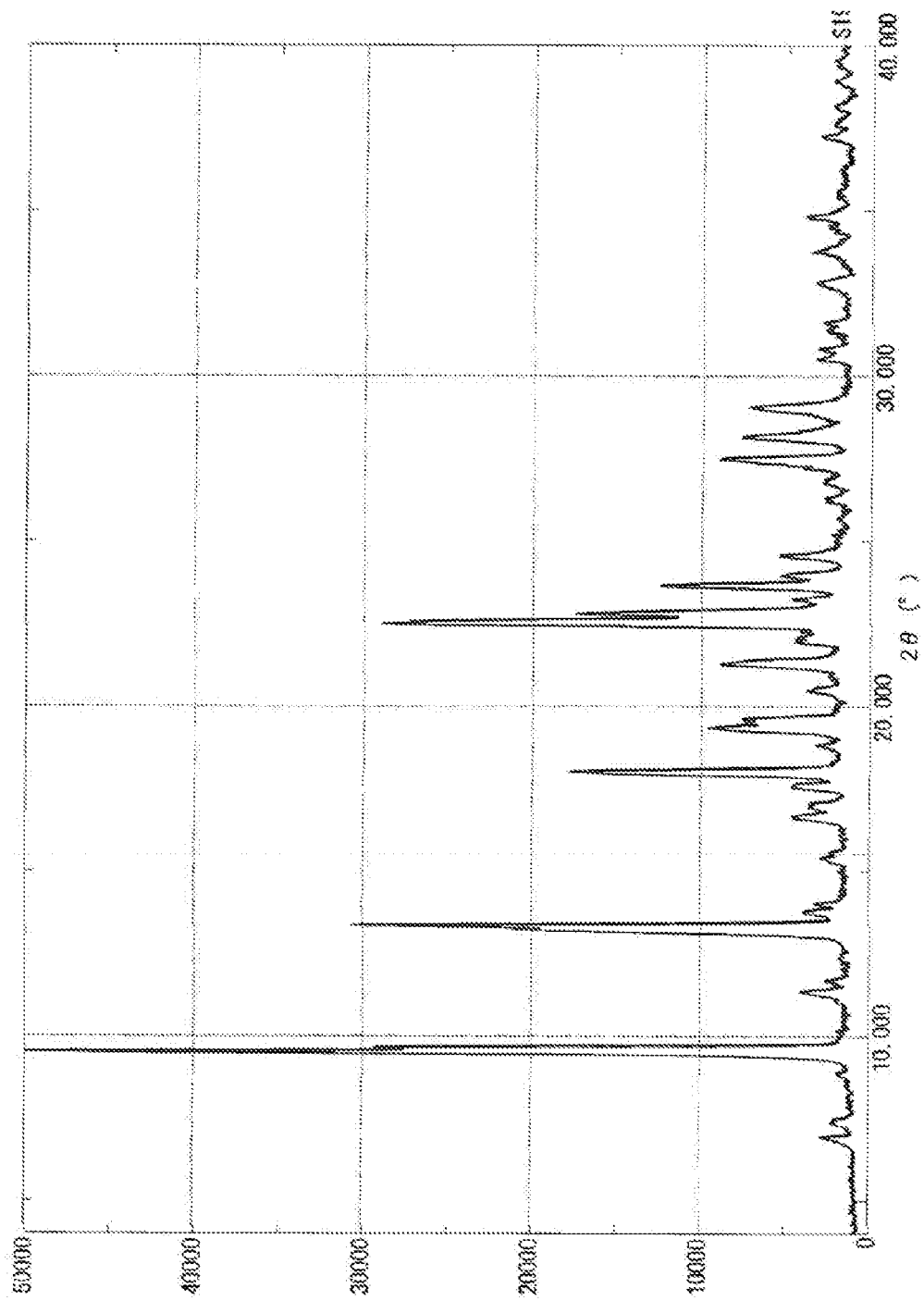
FIG. 2 is a powder X-ray diffraction pattern of Compound 9.

The powder X-ray diffraction pattern of Compound 9 is shown in FIG. 2.

Water content by Karl Fischer method: 2.8%

Example 3 Process of Compound 13

[Chem. 25]

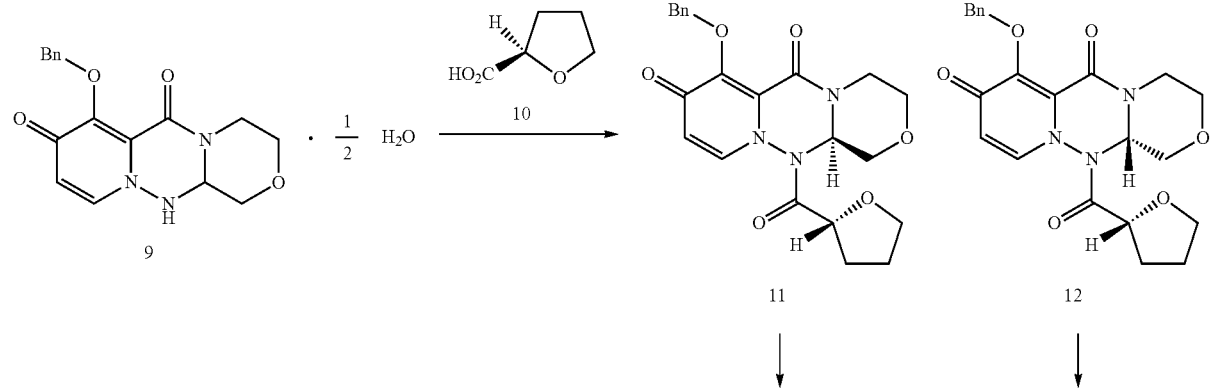

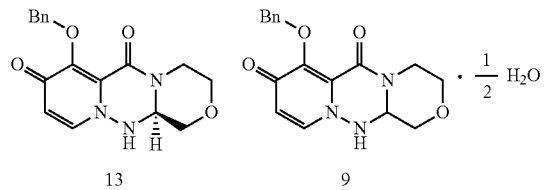

Step 1: Compounds 11 and 12

Ethyl acetate (87 mL) and 50 (w/w) % T3P ethyl acetate solution (145.80 g, 229.1 mmol) were added to 0.5 hydrate of compound 9 (30.00 g, 89.2 mmol), and the mixture was stirred. The reaction mixture was heated to 60° C., triethylamine (18.55 g, 183.3 mmol) was added, and then (R)-(+)-tetrahydrofuran-2-carboxylic acid (12.24 g, 105.4 mmol) was added slowly. The reaction mixture was stirred at 60° C. for 4.5 hours and then cooled to 0° C., and the resulting pale yellow precipitate was collected by filtration. The obtained solid was washed with ethyl acetate (120 mL) to obtain Compound 11 (18.34 g, undried) as a pale yellow solid. Also, the filtrate and the washing solution were combined to obtain an ethyl acetate solution of Compound 12 (358.60 g).

Step 2: Compounds 13 and 9

Ethyl acetate (120 mL) and 1,8-diazabicyclo[5.4.0]-7-undecene (530 mg, 3.5 mmol) were added to compound 11 (15.28 g), and the mixture was stirred. The reaction mixture was heated to 30° C., and a mixture of methanol (1.67 g) and ethyl acetate (43 mL) was added slowly. The reaction mixture was stirred at room temperature for 1 hour, and the resulting white precipitate was collected by filtration. The obtained crystals were washed with ethyl acetate (60 mL) and dried to obtain white crystals of compound 13 (11.06 g, yield 45%).

$^1$H-NMR (CDCl3) δ: 2.84-2.92 (m, 2H), 3.45 (td, J=3.2 Hz, 12.0 Hz, 1H), 3.82 (dd, J=4.0 Hz, 11.2 Hz, 1H), 3.92 (dd, J=4.4 Hz, 11.6 Hz, 1H), 4.13 (dd, J=2.8 Hz, 13.6 Hz, 1H), 4.47-4.54 (m, 1H), 4.96 (d, J=9.6 Hz, 1H), 5.27 (d, J=10.0 Hz, 1H), 5.76 (d, J=13.2 Hz, 1H), 6.19 (d, J=7.6 Hz, 1H), 7.22 (d, J=8.0 Hz, 1H), 7.30-7.38 (m, 3H), 7.59 (dd, J=1.6 Hz, 8.0 Hz, 2H).

Powder X-ray diffraction 2θ (°): 7.1, 14.1, 15.1, 21.0, 21.2, 22.9, 23.4

Figure 3:
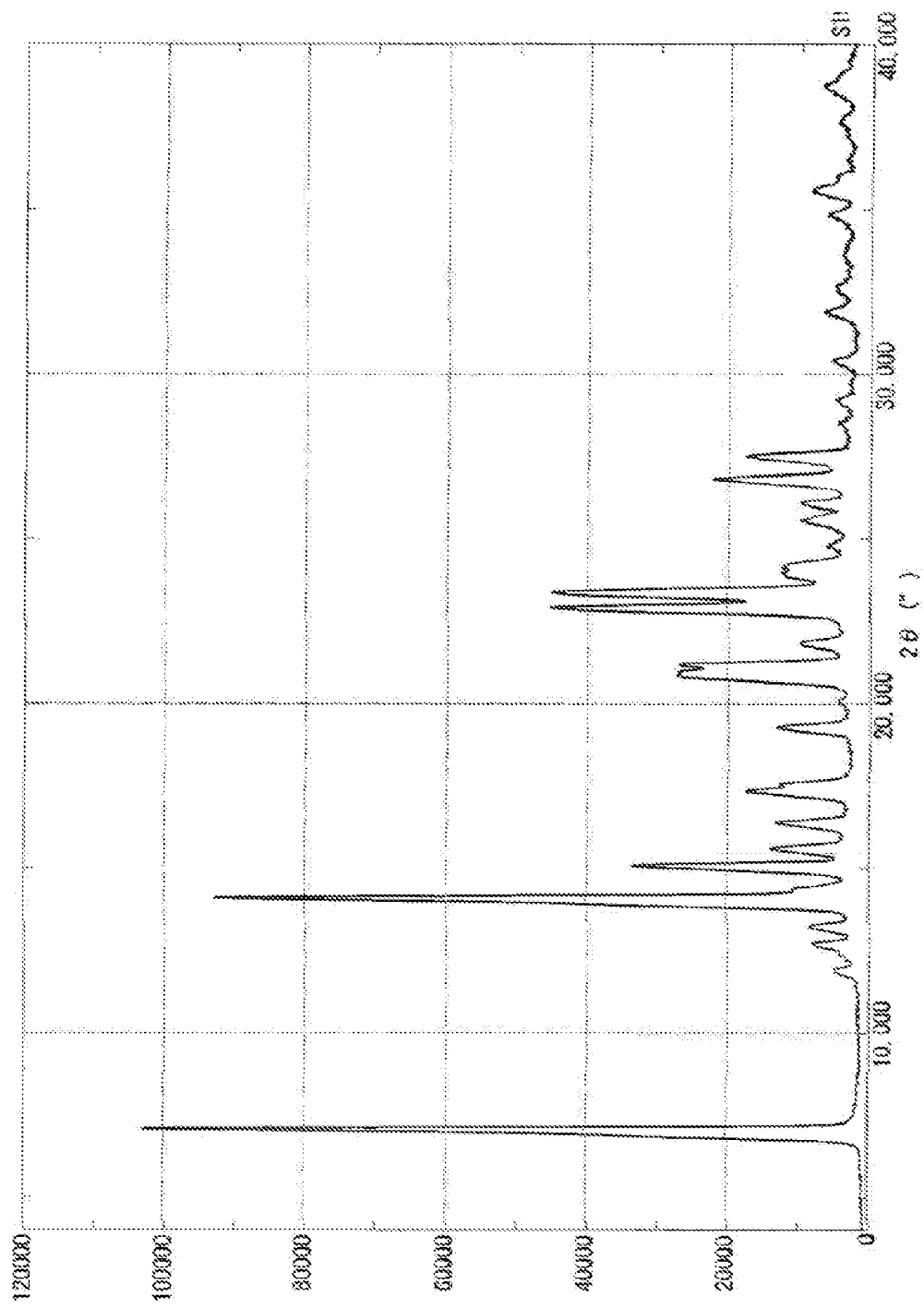
FIG. 3 is a powder X-ray diffraction pattern of Compound 13.

The powder X-ray diffraction pattern of Compound 13 is shown in FIG. 3.

A solution of compound 12 in ethyl acetate (334.69 g) was concentrated to about 170 g under reduced pressure. The concentrate solution was stirred at 25° C. Acetonitrile (224 mL), water (56 mL) and 24% aqueous sodium hydroxide solution (150 g) was added slowly to the mixture, and then separated into the organic layer and the aqueous layer. Water (14 mL) was added to the aqueous layer and extracted twice with acetonitrile (168 mL). The combined organic layer was concentrated to about 250 g under reduced pressure. The concentrate was heated to 60° C., and 1,8-diazabicyclo[5.4.0]-7-undecene (19.01 g, 124.9 mmol) was added. The reaction mixture was stirred at 60° C. for 3.5 hours and then cooled to 40° C. 5.8% aqueous hydrochloric acid (50.40 g) was added to the reaction mixture, and the resulting mixture was cooled to 25° C. to obtain a solution (314.96 g). A portion of the solution (158.86 g) was concentrated to about 85 g under reduced pressure. The concentrate was stirred at 20° C. for 2 hours, and water (28 mL) was added. The reaction mixture was concentrated to about 100 g under reduced pressure. After stirring the concentrate at 20° C. for 1 hour, the precipitated pale yellowish white crystals were collected by filtration. The obtained crystals were washed with water (42 mL) and dried to obtain Compound 9 (5.93 g, yield 42%) as pale yellowish white crystals.

Example 4: Compound 19

[Chem. 26]

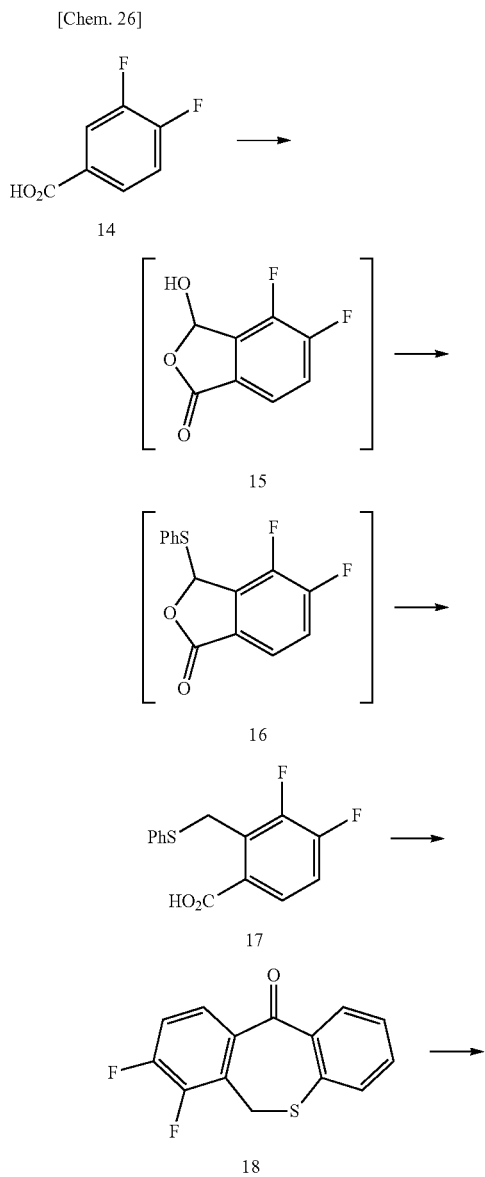

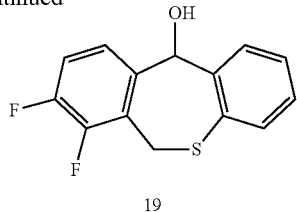

19

Step 1: Compound 15

Diisopropylamine (7.69 g, 76.0 mmol) was added to THF (25 mL), and the mixture was stirred and cooled to −40° C. After addition of 1.6 mol/L n-butyllithium (43.5 mL, 69.6 mmol), the resulting mixture was stirred at 0° C. for 1 hour. The mixture was cooled to −40° C., and a solution of 3,4-difluorobenzoic acid (5.00 g, 31.6 mmol) in THF (25 mL) was added slowly. The reaction mixture was stirred at −40° C. for 1 hour, and N,N-dimethylformamide (5.74 g, 78.5 mmol) was added slowly. To the reaction mixture was added 6 mol/L aqueous hydrochloric acid (34.25 mL), and the mixture was warmed to 25° C. and separated into the organic layer and the aqueous layer. The aqueous layer was extracted with ethyl acetate (15 mL). The combined organic layers was washed with water (5 mL). After concentration under reduced pressure, toluene was added to the residue to obtain a toluene solution of compound 15.

Step 2: Compound 16

Toluene (17.8 mL), thiophenol (3.90 g, 35.4 mmol) and D-camphorsulfonic acid (1.16 g, 5.0 mmol) were added to the above solution of compound 15. The mixture was stirred and heated to 60° C. The reaction mixture was stirred at 60° C. for 4 hours and then cooled to 5° C. 2 mol/L sodium hydroxide solution (10 mL) was added to the reaction mixture, and the resulting mixture was warmed to 25° C. The reaction mixture was extracted with toluene (10 mL), and the organic layer was washed with 2 mol/L sodium hydroxide (5 mL) and water (10 mL). After concentration of the organic layer under reduced pressure, toluene was added to obtain a toluene solution of compound 16.

Step 3: Compound 17

A mixture of aluminum chloride (5.52 g, 41.4 mmol) and toluene (25 mL) was stirred and cooled to 0° C. A solution of 1,1,3,3-tetramethyldisiloxane (5.56 g, 41.4 mmol) in toluene (10 mL) was added dropwise to the reaction mixture, and the mixture was warmed to 25° C. The above toluene solution of Compound 16 was added slowly to the reaction mixture, and the mixture was stirred at 25° C. for 2.5 hours. After addition of 15% sulfuric acid aqueous solution (35 mL), the mixture was stirred and then separated into the organic layer and the aqueous layer. The organic layer was washed twice with water (20 mL). The solution was concentrated to about 16 g under reduced pressure. Heptane (40 mL) was added slowly to the concentrate and cooled to 0° C. The resulting white precipitate was collected by filtration. The obtained solid was washed with heptane (20 mL) and then dried to obtain Compound 17 (7.20 g, yield 81.3%) as a white solid.

$^1$H-NMR (CDCl$_3$) δ:4.61 (d, J=1.6 Hz, 2H), 7.09-7.15 (m, 1H), 7.23-7.27 (m, 3H), 7.34-7.37 (m, 2H), 7.84-7.88 (m, 1H)

Step 4: Compound 18

Polyphosphoric acid (425.0 g) was stirred and heated to 80° C. Compound 17 (85.0 g) was added, and the mixture was warmed to 120° C. and stirred at 120° C. for 3 hours. The reaction mixture was cooled to 80° C., and water (200 mL) was added slowly. The reaction mixture was cooled to 30° C., and water (850 mL) was added. The mixture was extracted with ethyl acetate (850 mL). The organic layer was washed with water (425 mL) and 10% sodium hydrogen- carbonate aqueous solution (255 mL). The solvent was evaporated under reduced pressure, and heptane (340 mL) was added to the obtained residue. The solvent was evaporated under reduced pressure, and heptane (85 mL) was added to the obtained residue. After stirring the reaction mixture at 30° C. for 30 minutes, the resulting brown precipitate was collected by filtration. The obtained solid was washed with heptane (42 mL) and then dried to obtain Compound 18 (72.0 g, yield 91%) as a brown solid.

$^1$H-NMR (CDCl3) δ:4.14 (d, J=1.0 Hz, 2H), 7.09-7.18 (m, 1H), 7.27-7.33 (m, 1H), 7.34-7.45 (m, 3H), 8.19 (dd, J=8.5 Hz, 1.4 Hz, 1H)

Step 5: Compound 19

Sodium borohydride (234.0 mg, 6.2 mmol) was suspended in 0.5% sodium hydroxide aqueous solution (1.8 mL) to prepare a sodium borohydride suspension. 2-Propanol (20 mL) and water (2.25 mL) were added to compound 18 (4.5 g, 17.2 mmol). The mixture was stirred and heated to 40° C. The above sodium borohydride suspension was added slowly to the mixture. The reaction mixture was stirred at 40° C. for 1.5 hours and cooled to 25° C. Water (32 mL) was added to the reaction mixture, followed by addition of a mixed solution of water (6.7 mL) and 62% sulfuric acid aqueous solution (460 mg). The reaction mixture was cooled to 5° C., and the resulting brown precipitate was collected by filtration. The solid was washed with water (18 mL) and then dried to obtain Compound 19 (4.4 g, yield 97%) as a brown solid.

$^1$H-NMR (CDCl3) δ: 2.67 (d, J=3.8 Hz, 1H), 4.20 (dd, J=14.4, 1.4 Hz, 2H), 4.68 (dd, J=14.5, 1.3 Hz, 2H), 7.02 (dt, J=9.7, 8.3 Hz, 1H), 7.12-7.21 (m, 4H), 7.44-7.49 (m, 1H)

Example 5: Compounds (V) and (VI)

[Chem. 27]

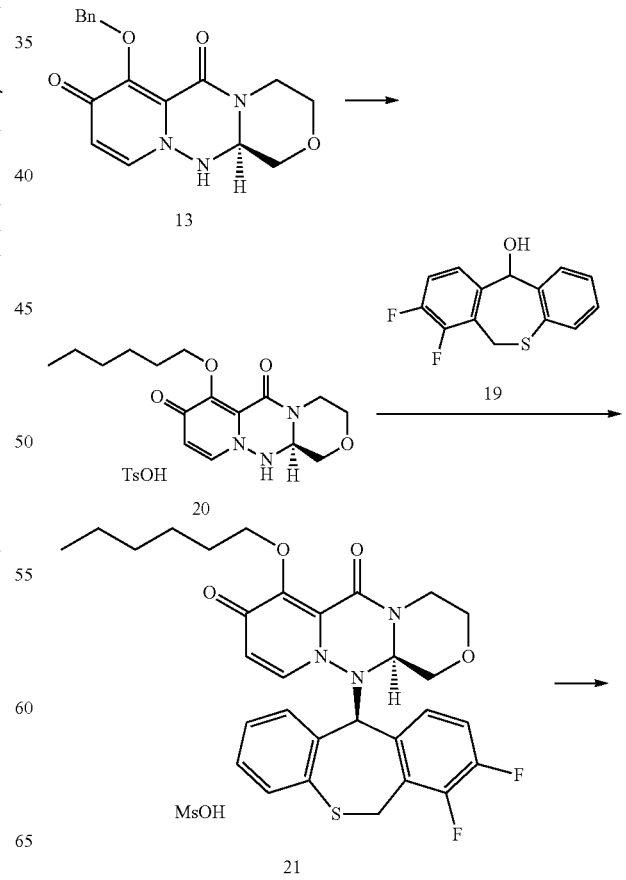

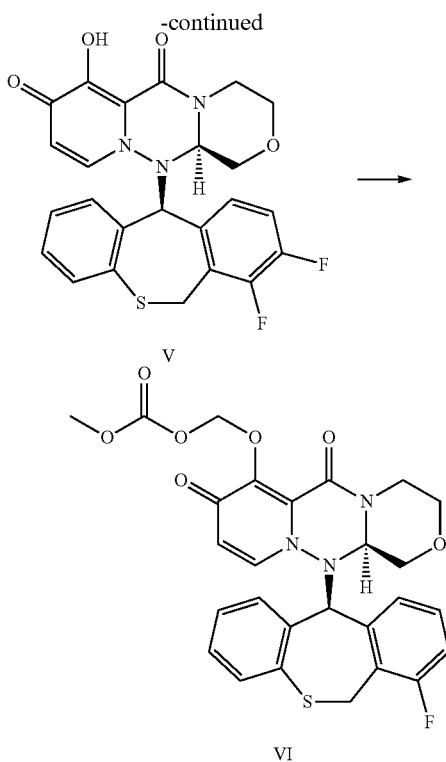

Step 1-1: Compound 20

1-Hexanol (22.5 g, 220 mmol) and THF (24.6 g) were combined, and the temperature of the mixture was adjusted to 20° C. A solution of isopropyl magnesium chloride in THF (2 mol/L, 7.2 g, 14.7 mmol) was added to the mixture to prepare a solution of magnesium hexoxide.

1-Hexanol (22.5 g, 220 mmol) was added to compound 13 (12.0 g, 36.7 mmol) with stirring, and the temperature of the mixture was adjusted to 20° C. The above magnesium hexoxide solution was added to the resulting slurry of compound 13. The reaction mixture was stirred at 20° C. for 4 hours, and then an aqueous solution of citric acid (3.1 g of citric acid monohydrate and 36 g of water) was added. The mixture was extracted with THF (10.7 g), and the organic layer was washed with water (24 g). The organic layer was concentrated to about 55 g under reduced pressure. A solution of p-toluenesulfonic acid in THF (7.0 g of p-toluenesulfonic acid monohydrate and 42.8 g of THF) was added to the resulting concentrate. The mixture was concentrated to about 61 g under reduced pressure. THF (42.7 g) was added to the concentrate, and the resulting mixture was concentrated to about 61 g under reduced pressure. After heating the mixture to 50° C., methyl tert-butyl ether (133.0 g) was added. The resulting mixture was cooled to 10° C., and stirred at 10° C. for 1.5 hours. The resulting white precipitate was collected by filtration. The obtained solid was washed with a mixture of methyl tert-butyl ether (40.0 g) and ethyl acetate (16.0 g), and dried to obtain the tosylate of compound 20 (15.8 g, yield 87.2%) as white crystals.

$^1$H-NMR (CDCl$_3$) δ: 0.88 (t, J=7.2 Hz, 3H), 1.25-1.34 (m, 4H), 1.34-1.43 (m, 2H), 1.76-1.85 (m, 2H), 2.34 (s, 3H), 3.04 (ddd, J=13.6, 11.7, 4.3 Hz, 3H), 3.36 (dd, J=11.6, 10.0 Hz, 3H), 3.43 (ddd, J=13.6, 12.0, 4.4 Hz, 3H), 4.00 (dd, J=11.7, 4.3 Hz, 1H), 4.06-4.18 (m, 4H), 4.80 (br, s, 1H), 7.16 (d, J=7.8 Hz, 1H), 7.62 (d, J=7.8 Hz, 1H), 7.62 (d, J=7.1 Hz, 1H), 8.17 (d, J=7.1 Hz, 1H), 8.40 (br, s, 1H).

Powder X-ray diffraction 2θ (°): 5.9, 8.4, 11.6, 12.7, 13.1, 15.7

Figure 4:
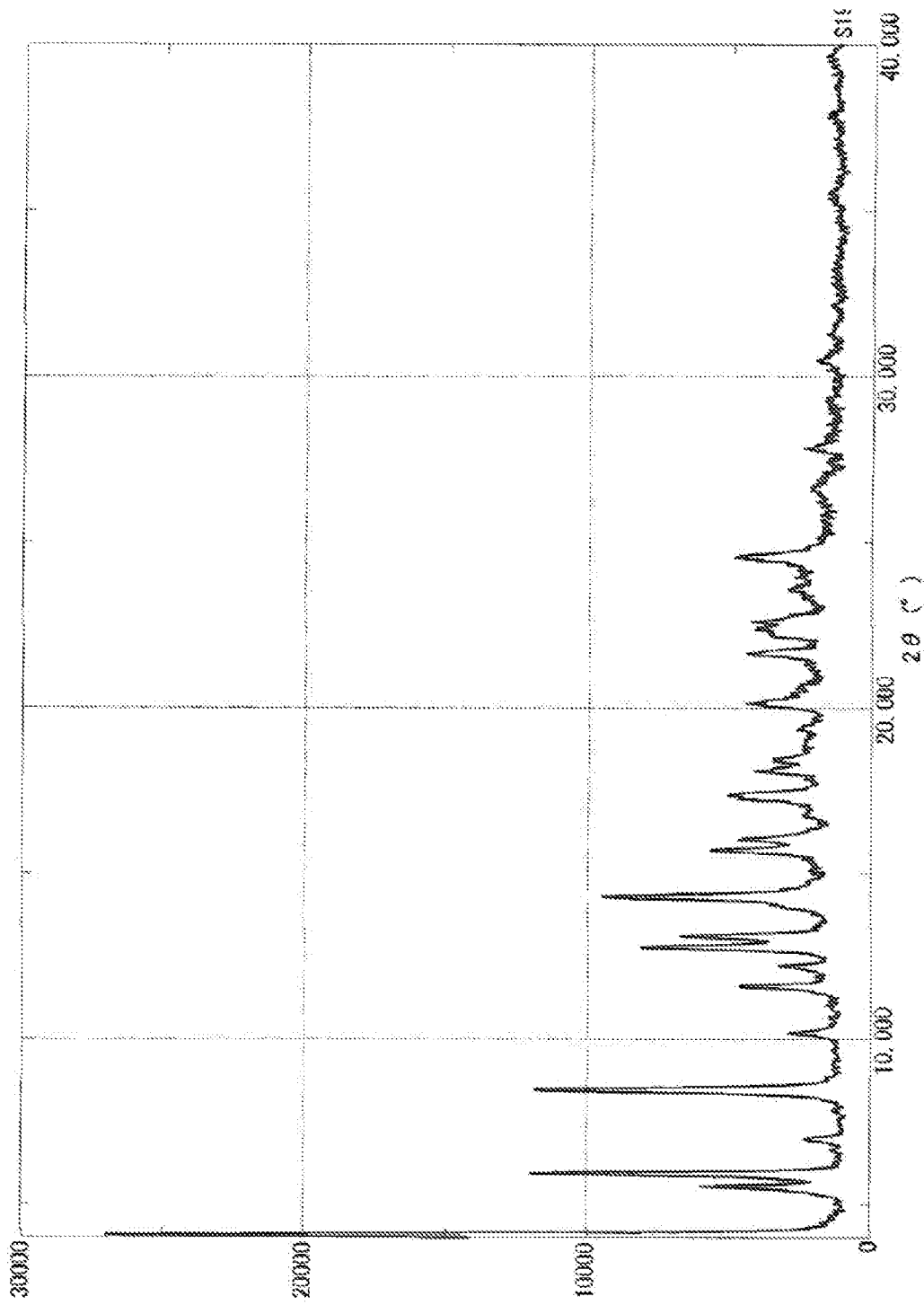
FIG. 4 is a powder X-ray diffraction pattern of a tosylate of Compound 20.

The powder X-ray diffraction pattern of Compound 20 is shown in FIG. 4.

Step 1-2: Compound 20

A reaction was carried out as described in Step 1-1 using a solution of cyclohexylmagnesium chloride in THF (16.2 wt %, 0.4 eq) instead of the solution of isopropylmagnesium chloride in THF (0.4 eq), and the reaction mixture was analyzed by HPLC to determine the formation rate of compound 20.

HPLC area percentage of compound 20: 90.9% (RT=11.0 min) The other procedures were the same as described in Step 1-1.

(Measurement Condition)
(1) Column: X Select™ CSH C18 (3.5 μm i.d. 4.6×100 mm) (Waters)
Flow rate: 1.0 mL/min; UV detection wavelength: 254 nm;
Mobile Phase:
  [A] 0.1% formic acid aqueous solution, [B] acetonitrile
  Gradient Program: (Concentration of [B]) 15%-15% 5 min; 15%-60% 10 min; 60%-85% 2 min; 85%-85% 3 min.

Step 1-3: Compound 20

1-Hexanol (27.5 g, 270 mmol) was added to compound 13 (4.91 g, 15.0 mmol), and the mixture was stirred. The temperature of the mixture was adjusted to 0° C. A solution of sodium tert-pentoxide in THF (1.4 mol/L, 45.0 mmol) was added to the resulting slurry. After stirring at 0° C. for 2.5 hours, the reaction mixture was analyzed by HPLC to determine the formation rate of compound 20.

HPLC area percentage of compound 20: 93.3% (RT=9.5 min)

(Measurement Condition)
(1) Column: CHIRALPAK™ IB (5.0 μm i.d. 4.6×250 mm) (DAICEL)
Flow rate: 1.0 mL/min; UV detection wavelength: 254 nm;
Mobile phase: [A] 0.1% formic acid, [B] acetonitrile
Gradient Program: maintained with 35% Solvent [B] for 5 min; linear gradient with 35% to 85% Solvent [B] over 6 min; and maintained with 85% Solvent [B] for 2 min.

As shown above, it was found that the reaction proceeded in good yield when using a magnesium salt or a sodium salt. The desired product was obtained in high yield, especially when using isopropyl magnesium chloride.

Step 2: Mesylate of Compound 21

Compound 19 (8.0 g, 30.3 mmol), ethyl acetate (48.7 g) and cyclohexane (14.1 g) were added to compound 20 (12.0 g, 24.3 mmol), and the mixture was stirred at 25° C. 50 (w/w) % T3P ethyl acetate solution (20.91 g, 32.9 mmol) was added followed by addition of methanesulfonic acid (3.5 g, 36.4 mmol). The mixture was heated to 60° C. and stirred for 24 hours. After cooling to 25° C., THF (32.0 g) and water (24.0 g) were added, and then 24% sodium hydroxide aqueous solution (30.8 g) was added slowly. After settling, the mixture was separated into the organic layer and the aqueous layer. The organic layer was washed twice with 7% sodium chloride aqueous solution (60.0 g). A solution of methanesulfonic acid (2.80 g, 29.1 mmol) in cyclohexane (9.3 g) and ethyl acetate (32.1 g) was added to the combined organic layer. The mixture was stirred at 25° C. for 2 hours, and the resulting white precipitate was collected by filtration. The obtained solid was washed with ethyl acetate (43.3 g) and then dried to obtain mesylate of compound 21 (13.65 g, yield 84.6%) as white crystals.

$^1$H-NMR (DMSO-d$_6$) δ: 0.90 (3H, t, J=6.0 Hz), 1.29-1.36 (4H, m), 1.39-1.49 (2H, m), 1.67-1.79 (2H, m), 2.38 (3H, s), 2.94 (1H, br s), 3.30 (1H, td, J=11.6, 2.4 Hz), 3.51 (1H, t, J=10.4 Hz), 3.66 (1H, dd, J=11.2, 2.8 Hz), 3.92-4.01 (2H, m), 4.07 (1H, d, J=14.3 Hz), 4.20 (1H, s), 4.42-4.52 (1H, m), 5.43 (1H, dd, J=14.4, 2.1 Hz), 5.79-5.83 (2H, m), 6.81 (1H, td, J=7.6, 1.2 Hz), 6.96 (1H, dd, J=7.8, 1.0 Hz), 7.09 (1H, J=8.0, 1.6 Hz), 7.12-7.18 (1H, m), 7.32 (1H, d, J=7.7 Hz), 7.37-7.49 (2H, m)

Powder X-ray diffraction 2θ (°): 7.1, 9.3, 12.6, 14.1, 17.7, 18.7, 19.2, 22.2, 25.4, 27.7, 28.5, 37.8

Figure 5:
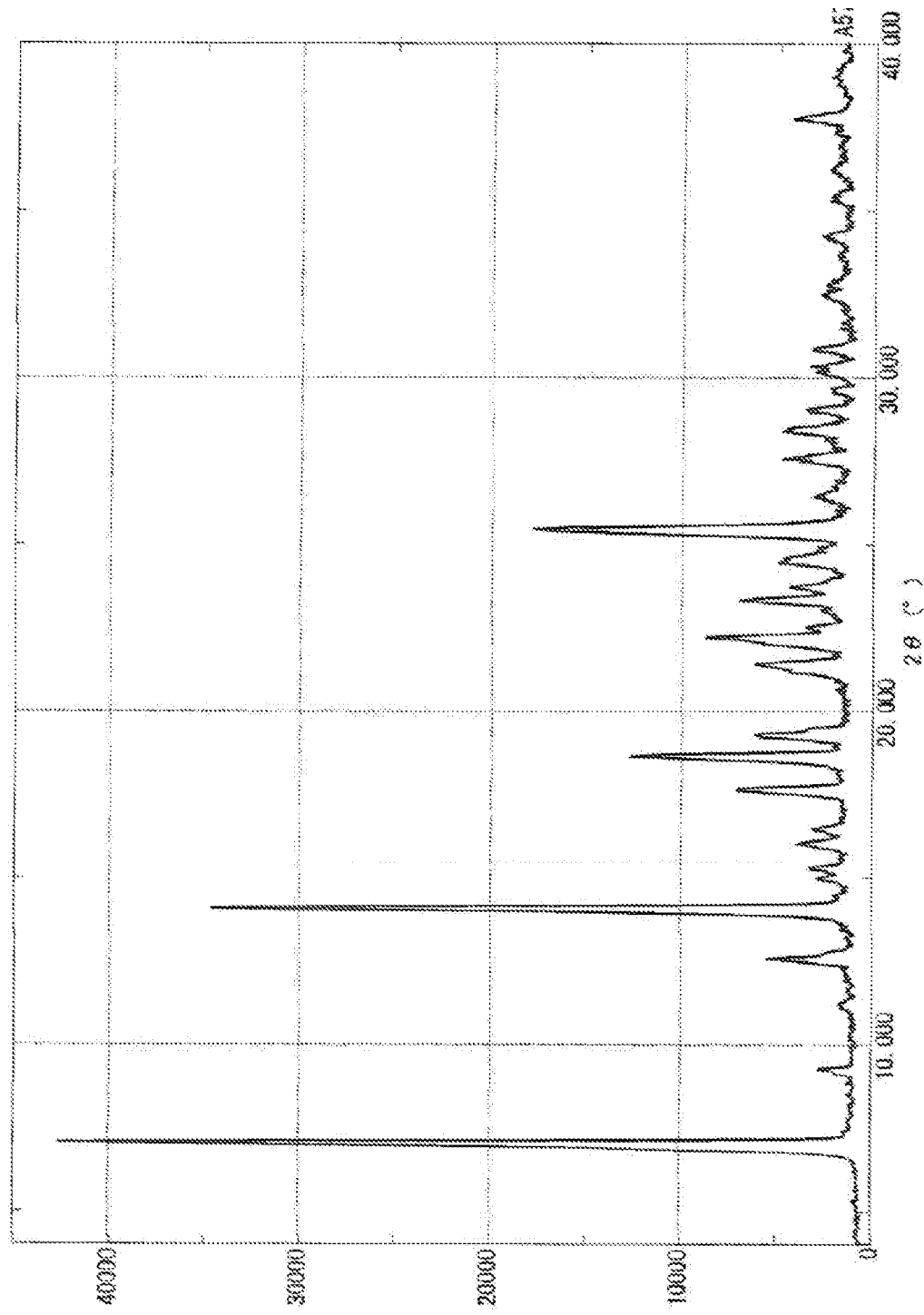
FIG. 5 is a powder X-ray diffraction pattern of a mesylate of Compound 21.

The powder X-ray diffraction pattern of Compound 21 is shown in FIG. 5.

DSC: Onset 216° C., Peak 219° C.

Step 3: Compound (V)

Lithium chloride (8.6 g, 203.3 mmol) was added to a mixture of N-methylpyrrolidone (52.4 g) and compound 21 (15.0 g, 22.6 mmol), and the resulting mixture was heated to 75° C. The mixture was stirred at 75° C. for 20 hours and then cooled to 40° C. Acetonitrile (20.0 g) was added to the reaction mixture, followed by addition of water (11.6 g). After cooling the mixture to 30° C. and stirring for 30 minutes, water (142.5 g) was added slowly. After stirring at 30° C. for 1.5 hours, the resulting white precipitate was collected by filtration. The solid obtained was washed with 2-propanol (60.1 g) and then dried to obtain Compound (V) (9.91 g, yield 90.7%) as white crystals.

$^1$H-NMR (CDCl3) δ: 3.00 (td, J=11.8, 3.2 Hz, 1H), 3.46 (td, J=12.0, 2.8 Hz, 1H), 3.59 (t, J=10.0 Hz, 1H), 3.82 (dd, J=12.2, 3.0 Hz, 1H), 3.96 (dd, J=11.0, 3.0 Hz, 1H), 4.07 (d, J=13.6 Hz, 1H), 4.58 (dd, J=10.0, 2.8 Hz, 1H), 4.67 (dd, J=13.6, 2.0 Hz, 1H), 5.26-5.30 (m, 2H), 5.75 (d, J=8.0 Hz, 1H), 6.69 (d, J=7.6 Hz, 1H), 6.83-6.87 (m, 1H), 6.99-7.04 (m, 2H), 7.07-7.15 (m, 3H).

Powder X-ray diffraction 2θ (°): 9.6, 10.9, 17.8, 21.5, 22.1, 23.5, 24.8

Figure 6:
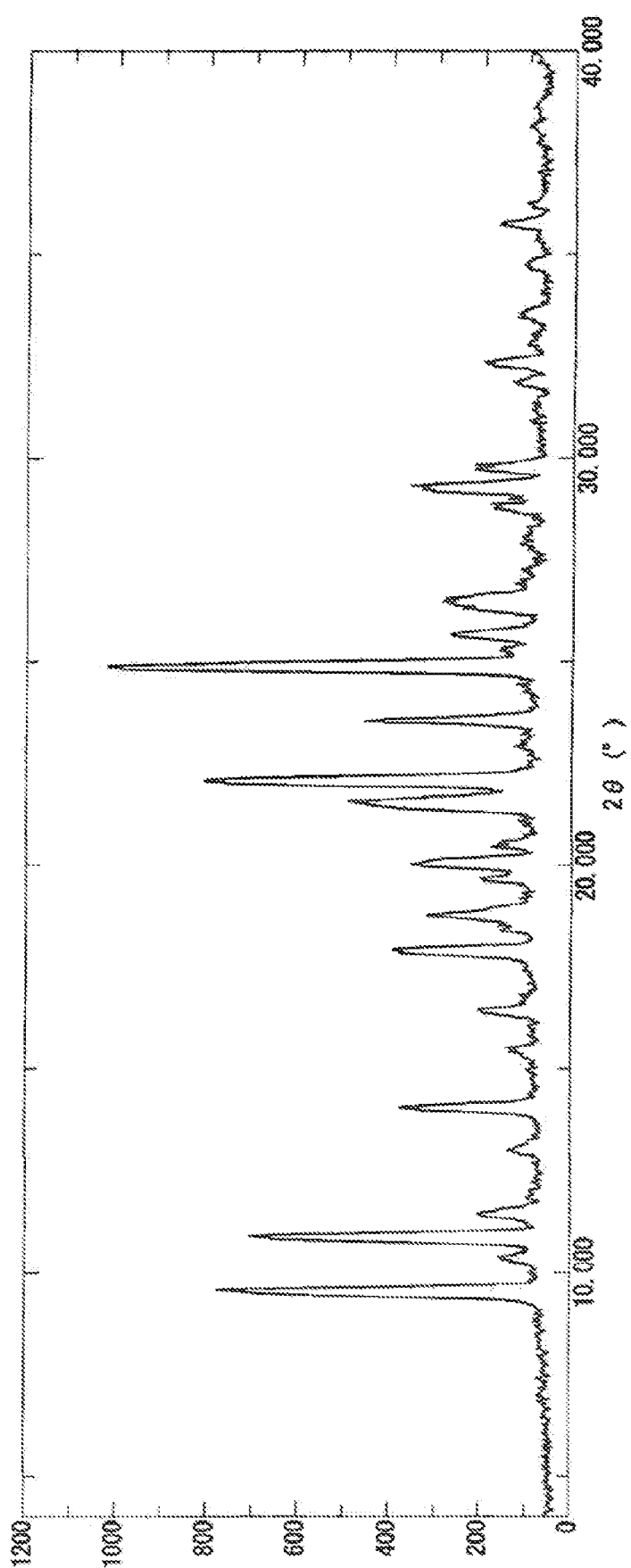
FIG. 6 is a powder X-ray diffraction pattern of Compound (V).

The powder X-ray diffraction pattern of Compound (V) is shown in FIG. 6.

Step 4: Compound (VI)

Chloromethyl methyl carbonate (0.483 g, 3.10 mmol), potassium carbonate (0.572 g, 4.14 mmol) and potassium iodide (0.343 g, 2.07 mmol) were mixed with a suspension of Compound (V) (1.00 g, 2.07 mmol) in DMA (5 ml). The mixture was heated to 50° C. and stirred for 6 hours. DMA (1 ml) was added to the reaction mixture, and the resulting mixture was stirred for 6 hours. The reaction mixture was cooled to room temperature, and DMA (6 ml) was added. The mixture was stirred at 50° C. for 5 minutes and then filtered. 1 mol/L hydrochloric acid (10 ml) and water (4 ml) were added dropwise to the obtained filtrate under ice cooling, and then, the mixture was stirred for 1 hour. The precipitated solid was collected by filtration and dried under reduced pressure at 60° C. for 3 hours to obtain Compound (VI) (1.10 g, 1.93 mmol, yield 93%).

$^1$H-NMR (DMSO-D6) δ: 2.91-2.98 (1H, m), 3.24-3.31 (1H, m), 3.44 (1H, t, J=10.4 Hz), 3.69 (1H, dd, J=11.5, 2.8 Hz), 3.73 (3H, s), 4.00 (1H, dd, J=10.8, 2.9 Hz), 4.06 (1H, d, J=14.3 Hz), 4.40 (1H, d, J=11.8 Hz), 4.45 (1H, dd, J=9.9, 2.9 Hz), 5.42 (1H, dd, J=14.4, 1.8 Hz), 5.67 (1H, d, J=6.5 Hz), 5.72-5.75 (3H, m), 6.83-6.87 (1H, m), 7.01 (1H, d, J=6.9 Hz), 7.09 (1H, dd, J=8.0, 1.1 Hz), 7.14-7.18 (1H, m), 7.23 (1H, d, J=7.8 Hz), 7.37-7.44 (2H, m).

$^1$H-NMR (DMSO-D$_6$) δ: 2.91-2.98 (1H, m), 3.24-3.31 (1H, m), 3.44 (1H, t, J=10.4 Hz), 3.69 (1H, dd, J=11.5, 2.8 Hz), 3.73 (3H, s), 4.00 (1H, dd, J=10.8, 2.9 Hz), 4.06 (1H, d, J=14.3 Hz), 4.40 (1H, d, J=11.8 Hz), 4.45 (1H, dd, J=9.9, 2.9 Hz), 5.42 (1H, dd, J=14.4, 1.8 Hz), 5.67 (1H, d, J=6.5 Hz), 5.72-5.75 (3H, m), 6.83-6.87 (1H, m), 7.01 (1H, d, J=6.9 Hz), 7.09 (1H, dd, J=8.0, 1.1 Hz), 7.14-7.18 (1H, m), 7.23 (1H, d, J=7.8 Hz), 7.37-7.44 (2H, m).

Example 6: Preparation of Compounds 33 to 41 and Diastereomeric Ratio of them

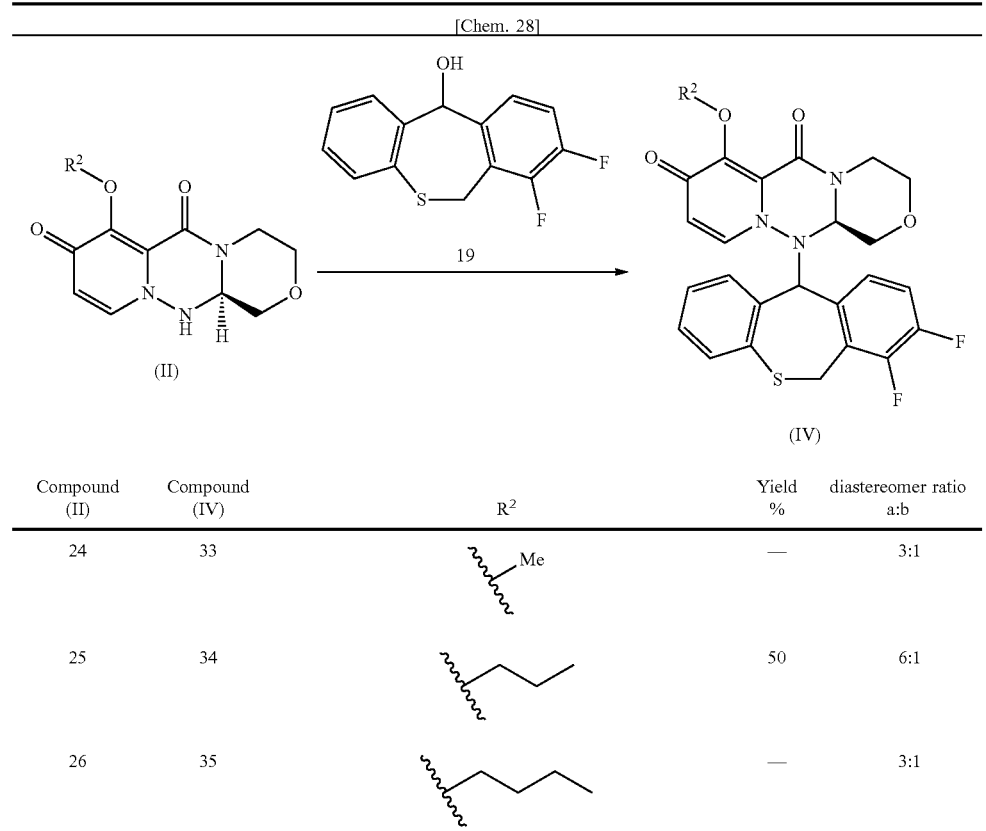

| Compound (II) | Compound (IV) | R² | Yield % | diastereomer ratio a:b |
|---|---|---|---|---|
| 24 | 33 | Me | — | 3:1 |
| 25 | 34 | (isobutyl) | 50 | 6:1 |
| 26 | 35 | (n-butyl) | — | 3:1 |

-continued

[Chem. 28]

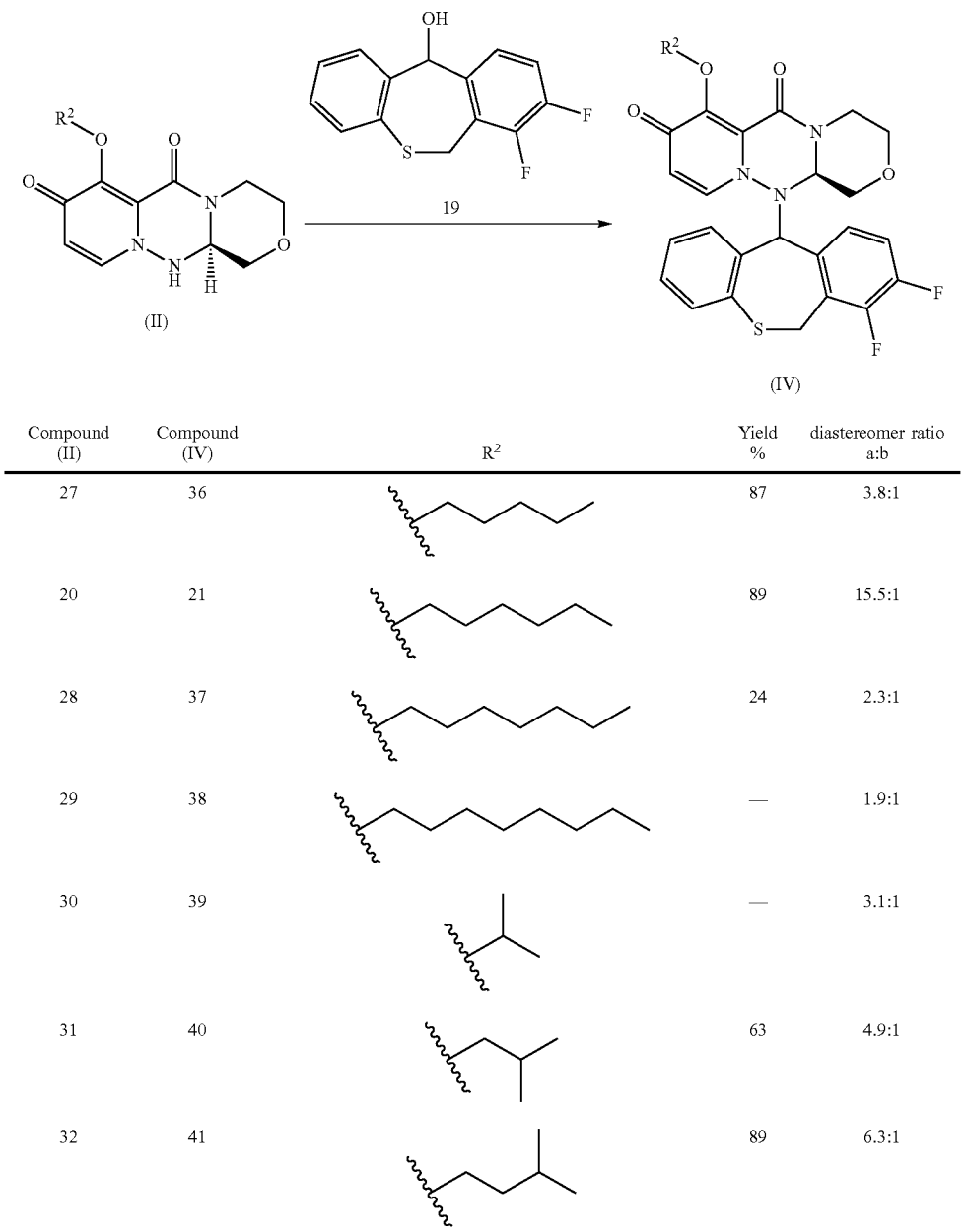

| Compound (II) | Compound (IV) | R² | Yield % | diastereomer ratio a:b |
|---|---|---|---|---|
| 27 | 36 | n-pentyl | 87 | 3.8:1 |
| 20 | 21 | n-hexyl | 89 | 15.5:1 |
| 28 | 37 | n-heptyl | 24 | 2.3:1 |
| 29 | 38 | n-octyl | — | 1.9:1 |
| 30 | 39 | isopropyl | — | 3.1:1 |
| 31 | 40 | isobutyl | 63 | 4.9:1 |
| 32 | 41 | isohexyl | 89 | 6.3:1 |

Step 1: Compounds 24 to 32

Compounds 24 to 32 were prepared according to Steps 1-1, 1-2, and 1-3 of Example 5, as well as conventional methods.

Step 2: Compounds 33 to 41

With procedure of Step 2 described in Example 5, each of Compounds 24 to 32 was reacted with Compound 19, and the reaction mixture was analyzed by HPLC to determine the diastereomer ratio of Compounds 33 to 41.

Compound 33a: tR 6.4 min/Compound 33b: tR 6.7 min
Compound 34a: tR 8.9 min/Compound 34b: tR 9.3 min
Compound 35a: tR 9.8 min/Compound 35b: tR 10.1 min
Compound 36a: tR 10.7 min/Compound 36b: tR 11.1 min
Compound 37a: tR 12.5 min/Compound 37b: tR 12.8 min
Compound 38a: tR 13.4 min/Compound 38b: tR 13.8 min
Compound 39a: tR 8.7 min/Compound 39b: tR 9.0 min
Compound 40a: tR 9.9 min/Compound 40b: tR 10.2 min
Compound 41a: tR 10.6 min/Compound 41b: tR 11.0 min (tR: retention time in HPLC measurement)

(Measurement Condition)

Column: KINETEX™ (2.6 μm C18 i.d. 4.6×100 mm) (Shimadzu)

Flow rate: 1.0 mL/min; UV detection wavelength: 254 nm;

Mobile phase: [A] 0.1% formic acid aqueous solution, [B] 0.1% formic acid in acetonitrile Gradient Program: started with 25% Solvent [B]; linear gradient with 25% to 70% Solvent [B] over 10 min; and maintained with 70% Solvent [B] for 8 min.

Test Example 1: Measurement of Cap-Dependent Endonuclease (CEN) Inhibitory Activity 1) Preparation of Substrate 30merRNA (5'-pp-[m2'-O]GAA UAU(-Cy3) GCA UCA CUA GUA AGC UUU GCU CUA-BHQ2-3', Japan Bioservice), wherein G at the 5' end has been diphosphate-modified, the hydroxy group at 2' position has been methoxylation-modified, U at the sixth position from the 5' end has been labelled with Cy3, and the 3' end has been labelled with BHQ2, was purchased, and a cap structure was added using ScriptCap system manufactured by EPICENTRE to give the product m7G [5']-ppp-[5'] [m2'-O]GAA UAU(-Cy3) GCA UCA CUA GUA AGC UUU GCU CUA (-BHQ2)-3'). The product was isolated and purified by denatured polyacrylamide gel electrophoresis, and used as a substrate.

2) Preparation of Enzyme

RNP was prepared from a virus particle according to standard method (Reference: VIROLOGY (1976) 73, p 327-338 OLGA M. ROCHOVANSKY). Specifically, 10 days old embryonated chicken egg was inoculated with A/WSN/33 virus ($1\times10^3$ PFU/mL, 200 μL). After incubation at 37° C. for 2 days, the allantoic fluid of the chicken egg was recovered. A virus particle was purified by ultracentrifugation with 20% sucrose, solubilized with TritonX-100 and lysolecithin, and an RNP fraction (50-70% glycerol fraction) was collected by ultracentrifugation under density gradient with 30-70% glycerol, and was used as an enzyme solution (containing approximately 1 nM PB1/PB2/PA complex).

3) Enzymatic Reaction 2.5 μL of enzymatic reaction solution (53 mM Tris-hydrochloride (pH 7.8), 1 mM $MgCl_2$, 1.25 mM dithiothreitol, 80 mM NaCl, 12.5% glycerol, 0.15 μL of enzyme solution) was dispensed into a 384-well polypropylene plate. Then, 0.5 μL of a test compound solution which has been serially diluted with dimethyl sulfoxide (DMSO) was added to the plate. For positive control (PC) and negative control (NC), 0.5 μL of DMSO was added to the plate, respectively. The solutions were mixed well. Then, 2 μL of substrate solution (1.4 nM substrate RNA, 0.05% Tween 20) was added to initiate the reaction. After incubation at room temperature for 60 minutes, 1 μL of the reaction solution was added to 10 μL of Hi-Di formamide solution (containing GeneScan 120 Liz Size Standard as a sizing marker: manufactured by Applied Biosystem (ABI)) to quench the reaction. For NC, the reaction was quenched by adding EDTA (4.5 mM) in advance before the initiation of the reaction (the concentrations as indicated are final concentration).

4) Measurement of Inhibition Rate ($IC_{50}$ Value)

The reaction solution as quenched above was heated at 85° C. for 5 minutes and then rapidly cooled on ice for 2 minutes, and analyzed on ABI PRIZM 3730 Genetic Analyzer. The peak of the cap-dependent endonuclease product was quantified by the analysis software ABI Genemapper. The CEN reaction inhibition ratio (%) of the test compound was determined, with the fluorescence intensity of PC and NC being 0% inhibition and 100% inhibition, respectively, and the $IC_{50}$ values were determined using a curve fitting software (XLfit 2.0: Model 205 (IDBS)).

Test Example 2: CPE Suppression Effect

<Materials>

2% FCS E-MEM (prepared by adding kanamycin and FCS to MEM (Minimum Essential Medium) (Invitrogen))

0.5% BSA E-MEM (prepared by adding kanamycin and BSA to MEM (Minimum Essential Medium) (Invitrogen))

HBSS (hanks' Balanced Salt Solution)

MDBK cells (adjusted to appropriate cell number ($3\times10^5$/mL) with 2% FCS E-MEM)

MDCK cells (prepared by washing twice with HBSS and adjusted to appropriate cell number ($5\times10^5$/mL) with 0.5% BSA E-MEM)

Trypsin solution (Trypsin from porcine pancreas (SIGMA) was dissolved in PBS (−) and filtrated through a 0.45 μm filter)

EnVision (PerkinElmer)

WST-8 Kit (Kishida Chemical Co., Ltd.)

10% SDS solution

<Methods>

Diluting and Dispensing of Test Sample

As a culture medium, 2% FCS E-MEM was used for MDBK cells, and 0.5% BSA E-MEM was used for MDCK cells. Same culture medium was used for dilution of virus, cells and test samples.

The test sample was preliminarily diluted with a culture medium to an appropriate concentration, and a 2- to 5-fold serial dilution series was prepared (50 μL/well) in a 96-well plate. Two sets of the plate were prepared for anti-Flu activity measurement and cytotoxicity measurement, respectively. The measurements were performed in triplet for each drug.

When using MDCK cells for measurement of anti-Flu activity, Trypsin was added to the cells so that the final concentration was 3 ug/mL.

Diluting and Dispensing of Influenza Virus

Influenza viruses were diluted to an appropriate concentration with a culture medium and dispensed at 50 μL/well into 96-well plate containing the test sample. To the plate for measuring cytotoxicity, 50 μL/well of the culture solution was dispensed.

Dilution and Dispensing of Cells

The cells were diluted to appropriate cell number and dispensed at 100 μL/well to a 96-well plate containing test sample.

The cell culture was mixed using a plate mixer and incubated in a $CO_2$ incubator. The cells were cultured for 3 days for anti-Flu activity measurement and cytotoxicity measurement.

Dispensing of WST-8

A 96-well plate cultured for 3 days was observed with naked eye and under microscope to check the morphology of the cells and the presence or absence of crystals. The supernatant was removed so as not to inhale the cells from the plate.

A WST-8 Kit was diluted 10-fold with culture medium, and 100 μL of WST-8 solution was dispensed into each well. After mixing using a plate mixer, the cells were cultured in a $CO_2$ incubator for 1 to 3 hours.

For measuring anti-Flu activity, after the plate was incubated, 10% SDS solution (10 μL) was dispensed into each well to inactivate the virus.

Measurement of Absorbance

After mixing at 96-well plate, the absorbance was measured on EnVision at two wavelengths of 450 nm/620 nm.

<Calculation of Measurement Values>

The values were calculated using Microsoft Excel or a program having the equivalent calculation and processing ability, based on the following equation.

Calculation of effective concentration to achieve 50% influenza-infected cell death inhibition ($EC_{50}$)

$$EC_{50}=10^Z$$

$$Z=(50\%-\text{High }\%)/(\text{High }\%-\text{Low }\%)\times\{\log(\text{High conc.})-\log(\text{Low conc.})\}+\log(\text{High conc.})$$

The results of Test Example 1 and Test Example 2 for Compound (V) are shown below.

Test example 1 (CEN IC 50): 1.93 nM,
Test example 2 (CPE EC 50): 1.13 nM

The above results revealed that the compound of the formula (V) shows high cap-dependent endonuclease (CEN) inhibitory activity and/or high CPE inhibitory effect, and therefore, is useful as a medicament for the treatment and/or prevention of symptoms and/or diseases induced by infection with influenza virus.

Biological test examples of Compounds (V) and (VI) are described below.

Test Example 3: CYP Inhibition Test

Using commercially available pooled human hepatic microsome and employing, as a reference, typical substrate metabolism reactions of human main five CYP enzyme forms (CYP1A2, 2C9, 2C19, 2D6, 3A4), i.e., 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenedine hydroxylation (CYP3A4), the degree of inhibition by Compound (V) was assessed for each metabolite production.

The reaction conditions were as follows:

Substrate: 0.5 μmol/L ethoxyresorufin (CYP1A2), 100 μmol/L tolbutamide (CYP2C9), 50 μmol/L S-mephenytoin (CYP2C19), 5 μmol/L dextromethorphan (CYP2D6), 1 μmol/L terfenedine (CYP3A4); Reaction time: 15 minutes; Reaction temperature: 37° C.; Enzyme: pooled human hepatic microsome 0.2 mg protein/mL; Concentration of Compound (V): 1, 5, 10, 20 μmol/L (four points).

For each of the five substances, a reaction solution was prepared on a 96-well plate by adding the substrate, human hepatic microsome and Compound (V) to 50 mmol/L Hepes buffer in the proportion as described above. NADPH, which is a cofactor, was added to initiate the metabolism reaction. After incubating at 37° C. for 15 minutes, a methanol/acetonitrile solution (1/1 (v/v)) was added to quench the reaction. After centrifugation at 3000 rpm for minutes, resorufin (CYP1A2 metabolite) in the supernatant was measured by fluorescent multi-label counter, and hydroxytolbutamide (CYP2C9 metabolite), 4'-hydroxymephenytoin (CYP2C19 metabolite), dextrorphan (CYP2D6 metabolite) and terfenadine alcohol (CYP3A4 metabolite) were measured by LC/MS/MS.

As a control, DMSO (the solvent for dissolving Compound (V)) was added solely to the reaction system. The remaining activity (%) of Compound (V), relative to the control (100%), was calculated at each concentration of the compound, and the $IC_{50}$ was calculated by reverse presumption by a logistic model using the concentration and the inhibition rate.

(Result)
Compound (V): >20 μmol/L for the five enzyme forms

Test Example 4: BA Test

Materials and methods for studies on oral absorption
(1) Animal: mouse or SD rat
(2) Breeding condition: mouse or SD rat was allowed to freely take solid feed and sterilized tap water.
(3) Dose and grouping: orally or intravenously administered at a predetermined dose; grouping is as follows (Dose depends on the compound)
Oral administration: 1 to 30 mg/kg (n=2 to 3)
Intravenous administration: 0.5 to 10 mg/kg (n=2 to 3)
(4) Preparation of dosing solution: a solution or a suspension state for oral administration; a solubilized state for intravenous administration
(5) Administration method: forced gastric administration using oral probe for oral administration; administration from caudal vein with a needle-equipped syringe for intravenous administration
(6) End point: blood was collected over time, and the plasma concentration of Compounds (V) and (VI) was measured by LC/MS/MS.
(7) Statistical analysis: regarding the transition of the plasma concentration of Compounds (V) and (VI), the area under the plasma concentration-time curve (AUC) was calculated by non-linear least squares program WinNonlin™, and the bioavailability (BA) of Compounds (V) and (VI) was calculated from the AUCs of the oral administration group and intravenous administration group.

(Result)
Compound (V): 4.2%
Compound (VI): 14.9%

The above results revealed that the prodrug has improved bioavailability over the parent compound.

Accordingly, the compound of the formula (VI) is excellent in oral absorption and is useful as a medicament in the treatment and/or prevention of symptoms and/or diseases induced by infection with influenza virus.

Test Example 5: Metabolism Stability Test

Compound (V) was reacted with commercially available pooled human hepatic microsomes for a certain time. The remaining rate of the compound was calculated by comparing the reacted sample and the unreacted sample to assess the degree of metabolism of Compound (V) in liver.

The compound was reacted in 0.2 mL of buffer (50 mmol/L Tris-HCl pH 7.4, 150 mmol/L potassium chloride, 10 mmol/L magnesium chloride) containing 0.5 mg protein/mL of human liver microsomes at 37° C. for 0 minute or 30 minutes in the presence of 1 mmol/L NADPH (oxidative reaction). After the reaction, 50 μL of the reaction solution was added to 100 μL of methanol/acetonitrile=1/1 (v/v), mixed and centrifuged at 3000 rpm for 15 minutes. The amount of Compound (V) in the supernatant was measured by LC/MS/MS, and the remaining rate of the compound after the reaction was calculated, with the amount of the compound at 0 minute of reaction time being 100%. The hydrolysis reaction was carried out in the absence of NADPH, and the glucuronidation reaction was carried out in the presence of 5 mmol/L UDP-glucuronic acid instead of NADPH, and the subsequent procedure was carried out in the same manner as described.

(Results)

The remaining rate in oxidative metabolism at 2 µmol/L of the compound is shown below.

Compound (V): 90.1%

Test Example 6: CYP3A4 Fluorescent MBI Test

The CYP3A4 fluorescent MBI test investigates enhancement of CYP3A4 inhibition by Compound (V) in metabolism reaction. 7-benzyloxytrifluoromethylcoumarin (7-BFC) was debenzylated by CYP3A4 enzyme (enzyme expressed in *Escherichia coli*) and a metabolite, 7-hydroxytrifluoromethylcoumarin (7-HFC) which emits fluorescent light was produced. The test was performed using 7-HFC production reaction as an index.

The reaction conditions were as follows: Substrate, 5.6 µmol/L 7-BFC; pre-reaction time, 0 or 30 minutes; reaction time, 15 minutes; reaction temperature, 25° C. (room temperature); CYP3A4 content (expressed in *Escherichia coli*), 62.5 µmol/mL at pre-reaction, 6.25 pmol/mL at reaction (at 10-fold dilution); concentration of Compound (V), 0.625, 1.25, 2.5, 5, 10, 20 µmol/L (six points).

A pre-reaction solution containing the enzyme and Compound (V) in K-Pi buffer (pH 7.4) as described above was added to a 96-well plate. A part of the solution was transferred to another 96-well plate and 1/10 diluted with a substrate and K-Pi buffer. NADPH, as a co-factor, was added to initiate the reaction (without pre-incubation), and acetonitrile/0.5 mol/L Tris (trishydroxyaminomethane)=4/1 (V/V) was added to quench the reaction after incubation for a predetermined time. Also, to another pre-incubation solution was added NADPH to initiate pre-incubation (with pre-incubation). After pre-incubation for a predetermined time, a part of the solution was transferred to another plate and 1/10 diluted with a substrate and K-Pi buffer to initiate reaction. After the reaction for a predetermined time, acetonitrile/0.5 mol/L Tris (trishydroxyaminomethane)=4/1 (V/V) was added to quench the reaction. For each of the plates on which the reaction was performed, the fluorescent value of the metabolite 7-HFC was measured by fluorescent plate reader (Ex=420 nm, Em=535 nm).

As a control for remaining activity, DMSO (i.e., the solvent for dissolving Compound (V)) was added solely to the reaction system, and the remaining activity (%) was calculated for each concentration of Compound (V) in the solution. The $IC_{50}$ value was calculated by reverse-presumption by logistic model using the concentration and the inhibition rate. A difference of 5 µM or more in the $IC_{50}$ values was defined as (+) and a difference of 3 µM or less was defined as (−)

(Results)

Compound (V): (−)

Test Example 7: Fluctuation Ames Test

The mutagenicity of Compound (V) was evaluated.

Each 20 µL of freeze-stored *Salmonella typhimurium* (TA98 and TA100 strain) was inoculated in 10 mL of liquid nutrient medium (2.5% Oxoid nutrient broth No. 2), and the cultures are incubated at 37° C. under shaking for 10 hours. The TA98 culture (9 mL) was centrifuged (2000×g, 10 minutes) to remove medium, and the bacteria was suspended in 9 mL of Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4·7H_2O$: 0.1 g/L). The suspension was added to 110 mL of Exposure medium (Micro F buffer containing Biotin: 8 µg/mL, histidine: 0.2 µg/mL, glucose: 8 mg/mL). The TA100 culture (3.16 mL) was added to 120 mL of Exposure medium to prepare the test bacterial solution. The test bacterial solution (588 µL), or in the case with metabolic activation system, a mixed solution of the test bacterial solution (498 µl) and the S9 mix (90 µL) was mixed with each 12 µL of the following solutions: Compound (V) in DMSO, serially diluted 2- or 3-fold in several steps from maximum dose 50 mg/mL; DMSO as negative control; 50 µg/mL of 4-nitroquinoline-1-oxide in DMSO as positive control for TA98 without metabolic activation system; 0.25 µg/mL of 2-(2-furyl)-3-(5-nitro-2-furyl)acrylamide in DMSO as positive control for TA100 without metabolic activation system; 40 µg/mL of 2-aminoanthracene in DMSO as positive control for TA98 with metabolic activation system; or 20 µg/mL of 2-aminoanthracene in DMSO as positive control for TA100 with metabolic activation system. The mixture was incubated at 37° C. under shaking for 90 minutes. The bacterial solution thus exposed to Compound (V) (460 µL) was added to 2300 µL of Indicator medium (Micro F buffer containing biotin: 8 µg/mL, histidine: 0.2 µg/mL, glucose: 8 mg/mL, Bromo Cresol Purple: 37.5 µg/mL), and each 50 µL of the mixture was dispensed into a microplate (48 wells per dose). After stationary cultivation at 37° C. for 3 days, a well containing bacteria, which has acquired a proliferative ability by mutation in the gene encoding amino acid (histidine) synthetase, turns the color from purple to yellow due to pH change. The number of the yellow wells among the 48 wells per dose was counted to evaluate the mutagenicity by comparing with the negative control group. (−) means that mutagenicity is negative and (+) means positive.

(Result)

Compound (V) (−)

Test Example 8: hERG Test

For the purpose of assessing risk of an electrocardiogram QT interval prolongation, effects of Compound (V) on delayed rectifier K+ current (IKr), which plays an important role in the ventricular repolarization process, was investigated using HEK293 cells expressing human ether-a-go-go related gene (hERG) channel.

Using an automated patch clamp system (PatchXpress 7000A, Axon Instruments Inc.), a cell was maintained at a membrane potential of −80 mV by whole cell patch clamp method. IKr induced by depolarization pulse stimulation at +40 mV for 2 seconds, and further, repolarization pulse stimulation at −50 mV for 2 seconds were recorded. After the generated current was stabilized, extracellular solution (NaCl: 135 mmol/L, KCl: 5.4 mmol/L, $NaH_2PO_4$: 0.3 mmol/L, $CaCl_2·2H_2O$: 1.8 mmol/L, $MgCl_2·6H_2O$: 1 mmol/L, glucose: 10 mmol/L, HEPES (4-(2-hydroxyethyl)-1-piperazine ethanesulfonic acid): 10 mmol/L, pH=7.4) containing Compound (V) at an objective concentration was applied to the cell at room temperature for 10 minutes. From the $I_{Kr}$ as recorded, absolute value of the tail peak current was determined on the basis of the current value at the resting membrane potential using an analysis software (DataXpress ver. 1, Molecular Devices Corporation). Further, the inhibition rate to the tail peak current before applying Compound (V) was calculated, and compared with the vehicle-applied group (0.1% dimethyl sulfoxide solution) to assess influence of Compound (V) on $I_{Kr}$.

(Result)

The inhibition rate at 0.3 to 10 µmol/L of the compound is shown below.

Compound (V): 7.9%

Test Example 9: Solubility Test

The solubility of Compound (V) was determined under 1% DMSO addition condition. A 10 mmol/L solution of the compound was prepared in DMSO, and 2 μL of Compound (V) solution was added respectively to 198 μL of JP-1 solution (sodium chloride 2.0 g, hydrochloric acid 7.0 mL and water to reach 1000 mL) and JP-2 solution (3.40 g of potassium dihydrogenphosphate and 3.55 g of disodium hydrogenphosphate anhydrous dissolved in water to reach 1000 mL, followed by adding 1 volume of which to 1 volume of water). After shaking at room temperature for 1 hour, the mixture was filtered. The filtrate was ten-fold diluted with methanol/water=1/1 (v/v), and the compound concentration in the filtrate was measured using LC/MS by absolute calibration method.
(Result)
Compound (V): 42.2 μmol/L

Test Example 10: Powder Solubility Test

Appropriate amounts of Compound (V) were put into appropriate containers. To the respective containers were added 200 μL of JP-1 solution (sodium chloride 2.0 g, hydrochloric acid 7.0 mL and water to reach 1000 mL), 200 μL of JP-2 solution (500 mL of water was added to 50 mL of phosphate buffer (pH 6.8)), and 200 μL of 20 mmol/L sodium taurocholate (TCA)/JP-2 solution (TCA 1.08 g and water to reach 100 mL). If Compound (V) was fully dissolved after addition to the test solution, Compound (V) was added further as appropriate. The containers were sealed, and shaken for 1 hour at 37° C. The mixtures were filtered, and 100 μL of methanol was added to each of the filtrate (100 μL) so that the filtrates were two-fold diluted. The dilution ratio was changed if necessary. The dilutions were observed for bubbles and precipitates, and then the containers were sealed and shaken. Quantification of Compound (V) was performed by HPLC with an absolute calibration method.
(Result)
Compound (V): JP-1 solution; 7.1 μg/mL, JP-2 solution 4.4 μg/mL, 20 mmol/L TCA/JP-2 solution 16.1 μg/mL

Test Example 11 Ames Test

Ames test was performed using Salmonellas (*Salmonella typhimurium*) TA 98, TA100, TA1535 and TA1537 and *Escherichia coli* WP2uvrA as a test strain with or without metabolic activation in the pre-incubation to check the presence or absence of gene mutagenicity of Compound (V).
(Result)
Compound (V): (−)

Test Example 12: Photohemolysis Test

Compound (V) was dissolved at a predetermined concentration and mixed on a microplate with a 0.1 to 0.0008% red blood cell suspension (2.5 v/v %) prepared from ovine defibrinated blood of sheep. Light irradiation in the UVA and UVB wavelength regions (10 J/cm$^2$, 290-400 nm) was performed using ultraviolet fluorescent lamp (GL20SE lamp, Sankyo Denki and FL20S-BLB lamp, Panasonic). The mixed solution after the irradiation was collected and centrifuged. After centrifugation, the supernatant was collected and transferred to a microplate, and the absorbance (at 540 or 630 nm) of the supernatant was measured. The absorbance at 540 and 630 nm were used as an index of biological membrane damage (% light hemolysis) and lipid membrane peroxidation (methemoglobin production), respectively. (−): less than 10% for photohemolysis rate and less than 0.05 for the change in absorbance at 630 nm; (+): 10% or more for photohemolysis rate and 0.05 or more for the change in absorbance at 630 nm.
(Result)
Compound (V): (−)

Figures 7, 8:
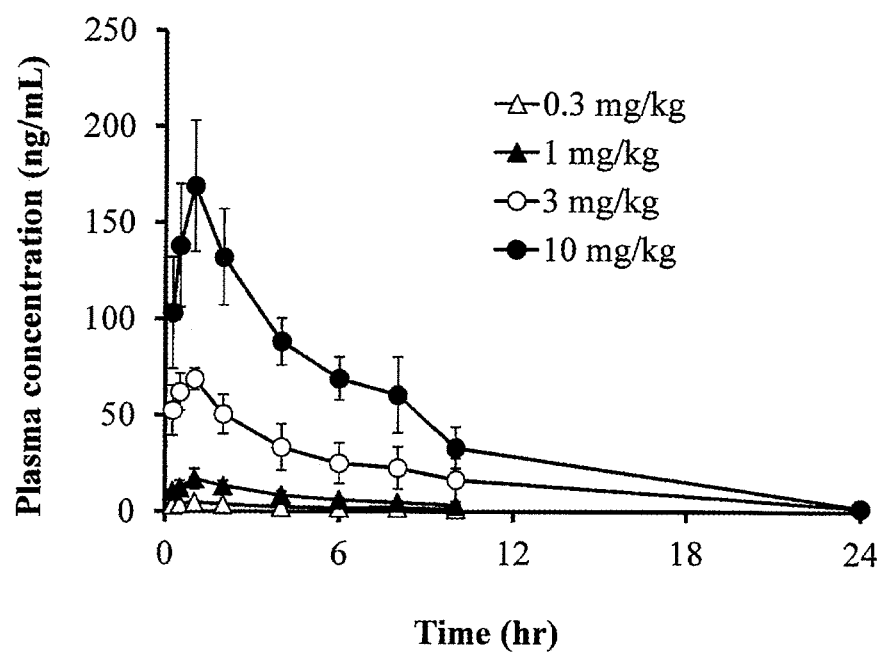
FIG. 7 is a time-course of the concentration in plasma of the compound of formula (V) after oral administration of the compound of formula (VI), which is a prodrug of the compound of formula (V), to rats under non-fasting condition.
FIG. 8 is a time-course of the concentration in plasma of the compound of formula (VI) after oral administration of the compound of formula (VI), which is a prodrug of the compound of formula (V), to rats under non-fasting condition.

FIG. 7 and FIG. 8 show the time-course of the concentration in plasma of Compound (V) and its prodrug Compound (VI) after oral administration of Compound (VI) to rats under non-fasting condition.

The concentration of Compound (VI) in plasma sample was below the limit of quantification, indicating that Compound (VI) which is a prodrug of Compound (V) was converted to Compound (V) in vivo rapidly after the administration (see FIG. 8).

These test results reveal that a prodrug compound was absorbed into the body after oral administration and rapidly converted to its parent compound in blood. Therefore, Compounds (V) and (VI) are useful as a medicament for the treatment and/or prevention of symptoms and/or diseases induced by infection with influenza virus.

Test Example 13: Intravenous Administration Test

Materials and Methods
 (1) Test animal: SD rats
 (2) Rearing conditions: SD rats allowed free access to solid feed and sterile tap water.
 (3) Dose and grouping setting: Intravenously administered according to a predetermined dosage. Groups were set up as follows (the dose may be changed for each compound). Intravenous administration: 0.5 to 1 mg/kg (n=2 to 3)
 (4) Preparation of administration liquid: Solubilized for intravenous administration.
 (5) Administration method: From the tail vein with a needle-equipped syringe.
 (6) End point: blood was collected over time, and the plasma concentration of Compounds (V) was measured by LC/MS/MS
 (7) Statistical Analysis: The total body clearance (CLtot) and elimination half-life (t½, z) were calculated using the nonlinear least squares program WinNonlin™ from the time-course of the concentration of Compound (V) in plasma.
(Result)
Compound (V):
CLtot: 16.4 mL/min/kg
t½, z: 3.4 hours The above results revealed that Compound (V) has a low whole-body clearance and a long half-life.

Accordingly, Compound (V) can be a drug that is excellent in persistence and useful as a medicament for the treatment and/or prevention of symptoms and/or diseases induced by infection with influenza virus.

The compound and the process of the present invention are useful as an intermediate for producing a useful compound as a medicament for the treatment and/or prevention of symptoms and/or diseases induced by infection with influenza virus. According to the method of the present invention, the compound of the formula (V) and the compound of the formula (VI) can be produced efficiently.

The invention claimed is:
1. A compound of the formula (II'):

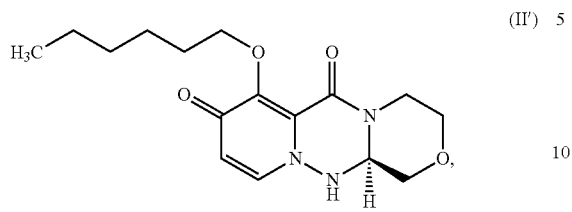

(II')

or a salt thereof.

2. A tosylate salt of the compound of formula (II') according to claim 1.

3. A crystal of the tosylate salt according to claim 2.

4. The crystal according to claim 3, comprising an X-ray powder diffraction pattern wherein the diffraction angles (2θ) of at least two peaks are selected from the group consisting of 5.9±0.2°, 8.4±0.2°, 11.6±0.2°, 12.7±0.2°, 13.1±0.2° and 15.7±0.2°.

5. The crystal according to claim 3, comprising an X-ray powder diffraction pattern comprising peaks at the diffraction angles (2θ) of 5.9±0.2°, 8.4±0.2°, 11.6±0.2°, 12.7±0.2°, 13.1±0.2° and 15.7±0.2°.

* * * * *